United States Patent [19]
Van den Berg et al.

[11] Patent Number: 4,943,529
[45] Date of Patent: Jul. 24, 1990

[54] KLUYVEROMYCES AS A HOST STRAIN

[75] Inventors: Johan A. Van den Berg, Ad Reeuwijk; Albert J. J. Van Ooyen, AR Voorburg; Krijn Rietveld, TL Vlaardingen, all of Netherlands

[73] Assignee: Gist-brocades NV, Delft, Netherlands

[21] Appl. No.: 78,539

[22] Filed: Jul. 28, 1987

Related U.S. Application Data

[63] Continuation-in-part of Ser. No. 572,414, Jan. 19, 1984, Pat. No. 4,859,596.

[51] Int. Cl.$^5$ .................... C12N 15/00; C12N 1/20; C12N 5/00
[52] U.S. Cl. ................... 435/172.3; 435/255; 435/256; 435/320; 435/91; 935/28; 935/37; 935/56
[58] Field of Search ............ 435/68, 20, 172.3, 226, 435/255, 64, 91, 240.1, 317, 253, 320, 317.1, 320; 935/28, 37, 56; 536/27

[56] References Cited

PUBLICATIONS

Ito et al. (1983) J. Bacteriology 153: pp. 163–168.

*Primary Examiner*—Robin Teskin
*Attorney, Agent, or Firm*—Barbara Rae-Venter

[57] ABSTRACT

Kluyveromyces hosts and DNA expression cassettes for use in Kluyveromyces are provided for transcription of endogenous and/or exogenous DNA, and production of peptides, for enhancing production of an endogenous product, or producing an exogenous product. The Kluyveromyces hosts find particular use for secretion of a desired peptide product, where signal sequences may be native to the peptide or provided from endogenous or exogenous signal sequences, including synthetic sequences, functional in Kluyveromyces. A transformation procedure is provided for efficiently transforming Kluyveromyces.

16 Claims, 33 Drawing Sheets

FIG. I
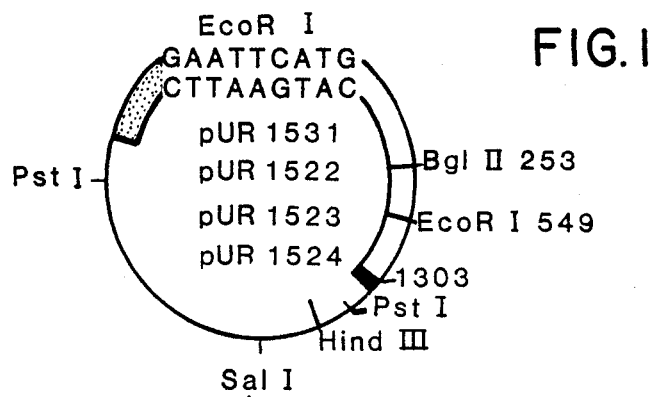
1. Partial EcoR I digestion (in the presence of ethidium bromide)
2. Sal I digestion
3. Purify EcoR I-Sal I fragments (1900-2150 bp) from agarose gel
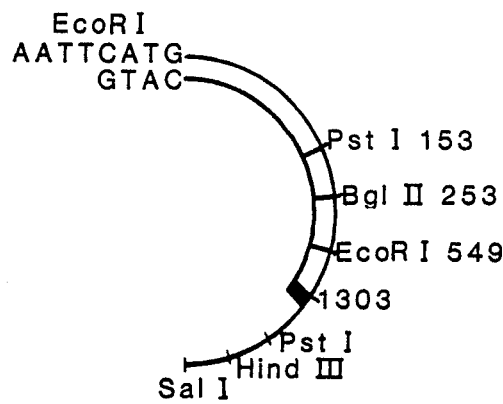
1) Fill-in cohesive ends with DNA polymerase (Klenow-fragment), 4 dNTP's
2) Add Sal I - linker (CGTCGACG / GCAGCTGC) with T4 DNA ligase, ATP
3) Hind III digestion
4) Sal I digestion
5) Purify Sal I - Hind III fragments from agarose gel
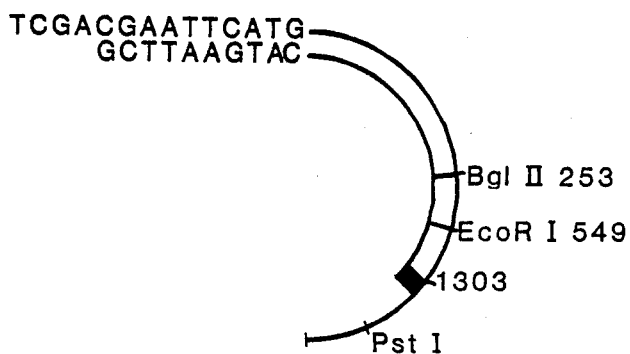
Fragments A, B, C, D

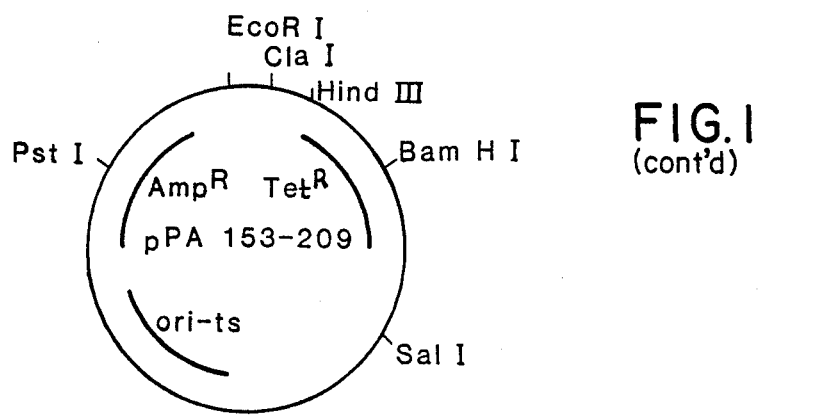
FIG. I
(cont'd)
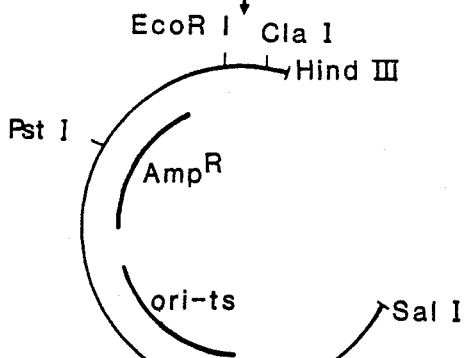
1. Hind III digestion
2. Sal I digestion
3. Purify 3.3 Kb fragment from agarose gel
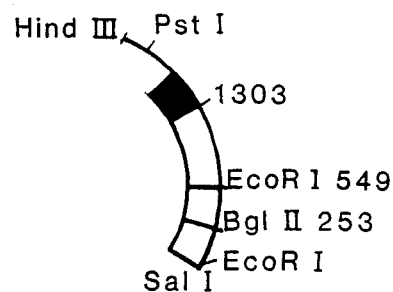
Fragments A, B, C, D
1. Ligation with T4 DNA ligase, ATP
2. Transformation into E. coli HB101
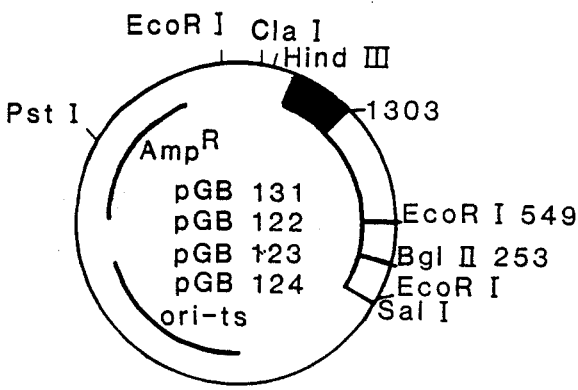

FIG. 3
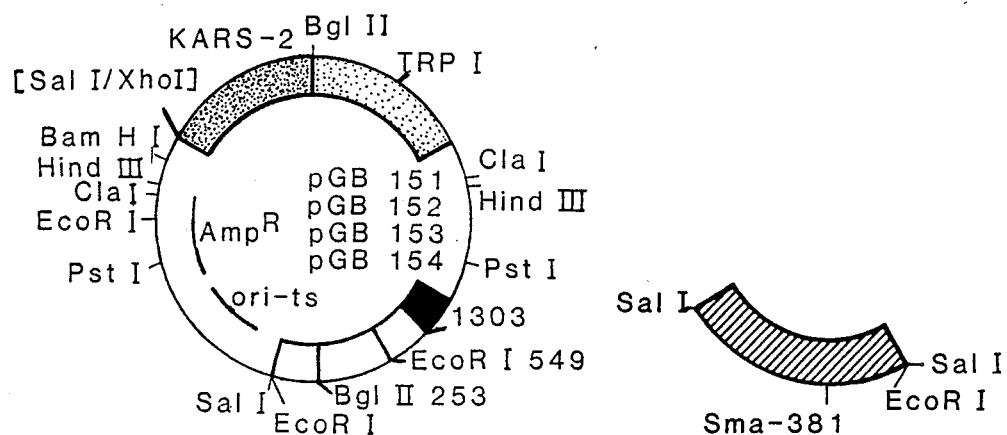
Sal I digestion
isocytochrome c I promotor fragment
1. ligation with T4 DNA ligase
2. transformation of E. coli HB 101
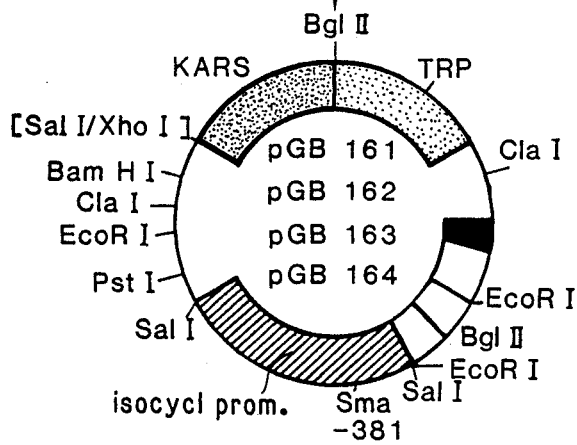

Oligonucleotides used for the synthesis of the amylo-glucosidase leader and protein sequence of the putative leader.

A (1) 5' TCGATATGTCTTTCAGATCCCTACTAGCTCTATCCG 3'

(2) 5' GTCTAGTTTGTACTGGTCTAGCTAACGTTATCTCCAAGAGAG 3'

(3) 5' TCGACTCTCTTGGAGATAACGTTAGCTAGACCAGTACAAACTAGACCGGATAG
AGCTAGTAGGGATCTGAAAGACATA 3'

B

Met Ser Phe Arg Ser Leu Leu Ala Leu Ser Gly Leu Val Cys Thr
Gly Leu Ala Asn Val Ile Ser Lys Arg

FIG. 5

Oligonucleotides used for the synthesis of the synthetic leader and protein sequence of the putative leader.

A (1) 5' TCGAATCTAATCTAAGTTTTAATTACAAAATGGCT 3'

(2) 5' TTCAGATCCTTGTTGGCTTTGTCCGGTTTGTCCTGTGGTGCTTTGGCTGCTCAAG 3'

(3) 5' TCGACTTGAGCAGCCAAAGCACCACAGGACAAACC 3'

(4) 5' GGACAAAGCCAACAAGGATCTGAAAGCCATTTTGTAATTAAAACTTAGATTAGAT 3'

B

Met Ala Phe Arg Ser Leu Leu Ala Leu Ser Gly Leu
Ser Cys Gly Ala Leu Ala Ala Glu

FIG. 6

```
  1 GGATCCCCAGCTTAGTTCATAGGTCCATTCTCTTAGCGCAACTACAGAGAACAGGGGCACAA
    CCTAGGGGTCGAATCAAGTATCCAGGTAAGAGAATCGCGTTGATGTCTCTTGTCCCCGTGTT

1 BAMHI,

63 ACAGGCAAAAAACGGGCACAACCTCAATGGAGTGATGCAACCTGCCTGGAGTAAATGATG
    TGTCCGTTTTTTGCCCGTGTTGGAGTTACCTCACTACGTTGGACGGACCTCATTTACTAC

123 ACACAAGGCAATTGACCCACGCATGTATCTATCTCATTTTCTTACACCTTCTATTACCTT
    TGTGTTCCGTTAACTGGGTGCGTACATAGATAGAGTAAAAGAATGTGGAAGATAATGGAA

183 CTGCTCTCTCTGATTTGGAAAAAGCTGAAAAAAAAGGTTGAAACCAGTTCCCTGAAATTA
    GACGAGAGAGACTAAACCTTTTTCGACTTTTTTTTCCAACTTTGGTCAAGGGACTTTAAT

236 XMNI,

243 TTCCCCTACTTGACTAATAAGTATATAAAGACGGTAGGTATTGATTGTAATTCTGTAAAT
    AAGGGGATGAACTGATTATTCATATATTTCTGCCATCCATAACTAACATTAAGACATTTA

303 CTATTTCTTAAACTTCTTAAATTCTACTTTTATAGTTAGTCTTTTTTTTAGTTTTAAAAC
    GATAAAGAATTTGAAGAATTTAAGATGAAAATATCAATCAGAAAAAAAATCAAAATTTTG

355 AHA3,

MetArgPheProSerIle
363 ACCAAGAACTTAGTTTCGAATAAACACACATAAACAAACACCATGAGATTTCCTTCAATT
    TGGTTCTTGAATCAAAGCTTATTTGTGTGTATTTGTTTGTGGTACTCTAAAGGAAGTTAA

377 ASU2,

PheThrAlaValLeuPheAlaAlaSerSerAlaLeuAlaAlaProValAsnThrThrThr
423 TTTACTGCAGTTTTATTCGCAGCATCCTCCGCATTAGCTGCTCCAGTCAACACTACAACA
    AAATGACGTCAAAATAAGCGTCGTAGGAGGCGTAATCGACGAGGTCAGTTGTGATGTTGT

427 PSTI,

GluAspGluThrAlaGlnIleProAlaGluAlaValIleGlyTyrLeuAspLeuGluGly
483 GAAGATGAAACGGCACAAATTCCGGCTGAAGCTGTCATCGGTTACTTAGATTTAGAAGGG
    CTTCTACTTTGCCGTGTTTAAGGCCGACTTCGACAGTAGCCAATGAATCTAAATCTTCCC

AspPheAspValAlaValLeuProPheSerAsnSerThrAsnAsnGlyLeuLeuPheIle
543 GATTTCGATGTTGCTGTTTTGCCATTTTCCAACAGCACAAATAACGGGTTATTGTTTATA
    CTAAAGCTACAACGACAAAACGGTAAAAGGTTGTCGTGTTTATTGCCCAATAACAAATAT

AsnThrThrIleAlaSerIleAlaAlaLysGluGluGlyValSerLeuAspLysArgAla
603 AATACTACTATTGCCAGCATTGCTGCTAAAGAAGAAGGGGTATCTCTAGATAAAAGAGCT
    TTATGATGATAACGGTCGTAACGACGATTTCTTCTTCCCCATAGAGATCTATTTTCTCGA

647 XBAI,

GAP/Alpha-Factor/Prochymosin Insert in pDM100PC

```
       GluIleThrArgIleProLeuTyrLysGlyLysSerLeuArgLysAlaLeuLysGluHis
  663  GAGATCACCAGGATCCCTCTGTACAAAGGCAAGTCTCTGAGGAAGGCGCTGAAGGAGCAT
       CTCTAGTGGTCCTAGGGAGACATGTTTCCGTTCAGAGACTCCTTCCGCGACTTCCTCGTA

673 BAMHI,

GlyLeuLeuGluAspPheLeuGlnLysGlnGlnTyrGlyIleSerSerLysTyrSerGly
  723  GGGCTTCTGGAGGACTTCCTGCAGAAACAGCAGTATGGCATCAGCAGCAAGTACTCCGGC
       CCCGAAGACCTCCTGAAGGACGTCTTTGTCGTCATACCGTAGTCGTCGTTCATGAGGCCG

741 PSTI, 772 SCAI,

PheGlyGluValAlaSerValProLeuThrAsnTyrProAspSerGlnTyrPheGlyLys
  783  TTCGGGGAGGTGGCCAGCGTCCCCCTGACCAACTACCCGGACAGTCAGTACTTTGGGAAG
       AAGCCCCTCCACCGGTCGCAGGGGGACTGGTTGATGGGCCTGTCAGTCATGAAACCCTTC

793 BALI, 829 SCAI, 841 BGL2,

IleTyrLeuGlyThrProProGlnGluPheThrValLeuPheAspThrGlySerSerAsp
  843  ATCTACCTCGGGACCCCGCCCCAGGAGTTCACCGTGCTGTTTGACACTGGCTCCTCTGAC
       TAGATGGAGCCCTGGGGCGGGGTCCTCAAGTGGCACGACAAACTGTGACCGAGGAGACTG

PheTrpValProSerMetTyrCysLysSerAsnAlaCysLysAsnHisGlnArgPheAsp
  903  TTCTGGGTACCCTCTATGTACTGCAAGAGCAATGCCTGCAAAAACCACCAGCGCTTCGAC
       AAGACCCATGGGAGATACATGACGTTCTCGTTACGGACGTTTTTGGTGGTCGCGAAGCTG

908 KPNI,

ProArgLysSerSerThrPheGlnAsnLeuGlyLysProLeuSerIleHisTyrGlyThr
  963  CCGAGAAAGTCGTCCACCTTCCAGAACCTGGGCAAGCCCCTGTCTATCCACTACGGGACA
       GGCTCTTTCAGCAGGTGGAAGGTCTTGGACCCGTTCGGGGACAGATAGGTGATGCCCTGT

983 PFLM1, 984 ALWN1,

GlySerMetGlnGlyIleLeuGlyTyrAspThrValThrValSerAsnIleValAspIle
 1023  GGCAGCATGCAGGGCATCCTGGGCTATGACACCGTCACTGTCTCCAACATTGTGGACATC
       CCGTCGTACGTCCCGTAGGACCCGATACTGTGGCAGTGACAGAGGTTGTAACACCTGTAG

1027 SPHI, 1050 TTH3I, 1066 BSTXI,

GlnGlnThrValGlyLeuSerThrAspGluProGlyAspValPheThrTyrAlaGluPhe
 1083  CAGCAGACAGTAGGCCTGAGCACCGACGAGCCCGGGACGTCTTCACCTATGCCGAATTC
       GTCGTCTGTCATCCGGACTCGTGGCTGCTCGGGCCCCTGCAGAAGTGGATACGGCTTAAG

1094 STUI, 1113 SMAI XMAI, 1119 AAT2, 1137 ECORI,

AspGlyIleLeuGlyMetAlaTyrProSerLeuAlaSerGluTyrSerThrSerValPhe
 1143  GACGGGATCCTGGGGATGGCCTACCCCTCGCTCGCCTCAGAGTACTCGACATCCGTGTTT
       CTGCCCTAGGACCCCTACCGGATGGGGAGCGAGCGGAGTCTCATGAGCTGTAGGCACAAA

1147 BAMHI, 1183 SCAI,
```

```
            AspAsnMetMetAsnArgHisLeuValAlaGlnAspLeuPheSerValTyrMetAspArg
1203        GACAACATGATGAACAGGCACCTGGTGGCCCAAGACCTGTTCTCGGTTTACATGGACAGG
            CTGTTGTACTACTTGTCCGTGGACCACCGGGTTCTGGACAAGAGCCAAATGTACCTGTCC

1221 DRA3,

AsnGlyGlnGluSerMetLeuThrLeuGlyProIleAspProSerTyrTyrThrGlySer
1263        AATGGCCAGGAGAGCATGCTCACGCTGGGGCCCATCGACCCGTCCTACTACACAGGGTCC
            TTACCGGTCCTCTCGTACGAGTGCGACCCCGGGTAGCTGGGCAGGATGATGTGTCCCAGG

1265 BAlI, 1276 SPHI, 1290 APAI,

LeuHisTrpValProValThrValGlnGlnTyrTrpGlnPheThrValAspSerValThr
1323        CTGCATTGGGTGCCCGTGACAGTGCAGCAGTACTGGCAGTTCACTGTGGACAGTGTCACC
            GACGTAACCCACGGGCACTGTCACGTCGTCATGACCGTCAAGTGACACCTGTCACAGTGG

1351 SCAI, 1371 TTH3I, 1380 HGIE2,

IleSerGlyValValValProCysGluGlyGlyCysGlnAlaIleLeuAspThrGlyThr
1383        ATCAGCGGTGTGGTTGTGCCCTGTGAGGGTGGCTGTCAGGCCATCCTGGACACGGGCACC
            TAGTCGCCACACCAACACGGGACACTCCCACCGACAGTCCGGTAGGACCTGTGCCCGTGG

SerLysLeuValGlyProSerSerAspIleLeuAsnIleGlnGlnProIleGlyAlaThr
1443        TCCAAGCTGGTCGGGCCCAGCAGCGACATCCTCAACATCCAGCAGCCCATTGGAGCCACA
            AGGTTCGACCAGCCCGGGTCGTCGCTGTAGGAGTTGTAGGTCGTCGGGTAACCTCGGTGT

1455 APAI,

GlnAsnGlnTyrGlyAspPheAspIleAspCysAspAsnLeuSerTyrMetProThrVal
1503        CAGAACCAGTACGGTGATTTTGACATCGACTGCGACAACCTGAGCTACATGCCCACTGTG
            GTCTTGGTCATGCCACTAAAACTGTAGCTGACGCTGTTGGACTCGATGTACGGGTGACAC

ValPheGluIleAsnGlyLysIleTyrProLeuThrProSerAlaTyrThrSerGlnAsp
1563        GTCTTTGAGATCAATGGCAAAATCTACCCACTGACCCCCTCCGCCTATACCAGCCAGGAC
            CAGAAACTCTAGTTACCGTTTTAGATGGGTGACTGGGGGAGGCGGATATGGTCGGTCCTG

GlnGlyPheCysThrSerGlyPheGlnSerGluAsnHisSerGlnLysTrpIleLeuGly
1623        CAGGGCTTCTGTACCAGTGGCTTCCAGAGTGAAAATCATTCCCAGAAATGGATCCTGGGG
            GTCCCGAAGACATGGTCACCGAAGGTCTCACTTTTAGTAAGGGTCTTTACCTAGGACCCC

1672 BAMHI,

AspValPheIleArgGluTyrTyrSerValPheAspArgProAsnAsnLeuValGlyLeu
1683        GATGTTTTCATCCGAGAGTATTACAGCGTCTTTGACAGGCCCAACAACCTCGTGGGGCTG
            CTACAAAAGTAGGCTCTCATAATGTCGCAGAAACTGTCCGGGTTGTTGGAGCACCCCGAC

1741 BAlI,

AlaLysAlaIleOP
1743        GCCAAAGCCATCTGATCTCGACTTGGTTGAACACGTTGCCAAGGCTTAAGTGAATTTACT
            CGGTTTCGGTAGACTAGAGCTGAACCAACTTGTGCAACGGTTCCGAATTCACTTAAATGA

1787 AFL2, 1802 AHA3,
```

1803 TTAAAGTCTTGCATTTAAATAAATTTTCTTTTTATAGCTTTATGACTTAGTTTCAATTTA
     AATTTCAGAACGTAAATTTATTTAAAAGAAAAATATCGAAATACTGAATCAAAGTTAAAT

1816 AHA3,

1863 TATACTATTTTAATGACATTTTCGATTCATTGATTGAAAGCTTTGTGTTTTTCTTGATG
     ATATGATAAAATTACTGTAAAAGCTAAGTAACTAACTTTCGAAACACAAAAAAGAACTAC

1900 HIND3,

1923 CGCTATTGCATTGTTCTTGTCTTTTTCGCCACATGTAATATCTGTAGTAGATACCTGATA
     GCGATAACGTAACAAGAACAGAAAAAGCGGTGTACATTATAGACATCATCTATGGACTAT

1983 CATTGTGGATGCTGAGTGAAATTTTAGTTAATAATGGAGGCGCTCTTAATAATTTTGGGG
     GTAACACCTACGACTCACTTTAAAATCAATTATTACCTCCGCGAGAATTATTAAAACCCC

2043 ATATTGGCTTTTTTTTTTAAAGTTTACAAATGAATTTTTTCCGCCAGGATAACGATTCTG
     TATAACCGAAAAAAAAAATTTCAAATGTTTACTTAAAAAAGGCGGTCCTATTGCTAAGAC

2058 AHA3, 2074 XMNI,

2103 AAGTTACTCTTAGCGTTCCTATCGGTACAGCCATCAAATCATGCCTATAAATCATGCCTA
     TTCAATGAGAATCGCAAGGATAGCCATGTCGGTAGTTTAGTACGGATATTTAGTACGGAT

2163 TATTTGCGTGCAGTCAGTATCATCTACATGAAAAAAACTCCCGCAATTTCTTATAGAATA
     ATAAACGCACGTCAGTCATAGTAGATGTACTTTTTTGAGGGCGTTAAAGAATATCTTAT

2223 CGTTGAAAATTAAATGTACGCGCCAAGATAAGATAACATATATCTAGCTAGATGCAGTAA
     GCAACTTTTAATTTACATGCGCGGTTCTATTCTATTGTATATAGATCGATCTACGTCATT

2283 TATACACAGATTCCCGCGGACGTGGGAAGGAAAAAATTAGATAACAAAATCTGAGTGATA
     ATATGTGTCTAAGGGCGCCTGCACCCTTCCTTTTTAATCTATTGTTTTAGACTCACTAT

2296 SAC2,

2343 TGGAAATTCCGCTGTATAGCTCATATCTTTCCCTTCAACACCAGAAATGTAAAAATCTTG
     ACCTTTAAGGCGACATATCGAGTATAGAAAGGGAAGTTGTGGTCTTTACATTTTTAGAAC

2403 TTACGAAGGATCTTTTTGCTAATGTTTCTCGCTCAATCCTCATTTCTTCCCTACGAAGAG
     AATGCTTCCTAGAAAAACGATTACAAAGAGCGAGTTAGGAGTAAAGAAGGGATGCTTCTC

2463 TCAAATCTACTTGTTTTCTGCCGGTATCAAGATCCATATCTTCTAGTTTCACCATCAAAG
     AGTTTAGATGAACAAAAGACGGCCATAGTTCTAGGTATAGAAGATCAAAGTGGTAGTTTC

2523 TCCAATTTCTAGTATACAGTTTATGTCCCAACGTAACAGACAATCAAAATTGGAAAGGAT
     AGGTTAAAGATCATATGTCAAATACAGGGTTGCATTGTCTGTTAGTTTTAACCTTTCCTA

2534 SNAI XCA1,

2583 AAGTATCCTTCAAAGAATGATTCTGCGCTGGCTCCTGAACCGCCTAATGGGAACAGAGAA
     TTCATAGGAAGTTTCTTACTAAGACGCGACCGAGGACTTGGCGGATTACCCTTGTCTCTT

2643 GTCCAAAACGATGCTATAAGAACCAGAAATAAAACGATAAAACCATACCAGGATCGGTCG
     CAGGTTTTGCTACGATATTCTTGGTCTTTATTTTGCTATTTTGGTATGGTCCTAGCCAGC

2689 HGIE2, 2699 SALI,

2703 ACTTTGTTCCCACTGTACTTTTAGCTCGTACAAAATACAATATACTTTTCATTTCTCCGT
     TGAAACAAGGGTGACATGAAAATCGAGCATGTTTTATGTTATATGAAAAGTAAAGAGGCA

2763 AAACAACATGTTTTCCCATGTAATATCCTTTTCTATTTTTCGTTCCGTTACCAACTTTAC
     TTTGTTGTACAAAAGGGTACATTATAGGAAAAGATAAAAAGCAAGGCAATGGTTGAAATG

2823 ACATACTTTATATAGCTATTCACTTCTATACACTAAAAAACTAAGACAATTTTAATTTTG
     TGTATGAAATATATCGATAAGTGAAGATATGTGATTTTTTGATTCTGTTAAAATTAAAAC

2883 CTGCCTGCCATATTTCAATTTGTTATAAATTCCTATAATTTATCCTATTAGTAGCTAAAA
     GACGGACGGTATAAAGTTAAACAATATTTAAGGATATTAAATAGGATAATCATCGATTTT

2943 AAAGATGAATGTGAATCGAATCCTAAGAGAATTCGGATCC
     TTTCTACTTACACTTAGCTTAGGATTCTCTTAAGCCTAGG

2971 ECORI, 2977 BAMHI,

Trp Ser Trp Ile Thr Leu

TGG QZV TGG ATL ACN YTI

CODE FOR AMBIGUOUS BASES:

Q: A OR T
R: A OR G
S: A OR C
Y: T OR C
Z: C OR G

L: A, T, OR C
N: ANY BASE
V: T OR

```
  1    CTGCAGTTTGTGAATCGTAAGACAGTGACATTTTTAGAGGTTGTTATCTGTTTAAGACGA
       GACGTCAAACACTTAGCATTCTGTCACTGTAAAAATCTCCAACAATAGACAAATTCTGCT

61    AATGGTTTGCTGTTCAAGCTCACTGGGTGATCGGATTTCGGGAAAATTCATATATAAAGG
       TTACCAAACGACAAGTTCGAGTGACCCACTAGCCTAAAGCCCTTTTAAGTATATATTTCC

1 PST1, 81 DRA3,

121    ACCCTTGATTGATAGGATGTTATGGTATTGTTCTAAGTTTGTTTCAATAGTAATTTCAAT
       TGGGAACTAACTATCCTACAATACCATAACAAGATTCAAACAAAGTTATCATTAAAGTTA

181    ATAGTATATTAGAACAAGCAAACCAGAGCATCTAAAGCCCAACTCGTCTGATCTTTTTCT
       TATCATATAATCTTGTTCGTTTGGTCTCGTAGATTTCGGGTTGAGCAGACTAGAAAAAGA

241    GTCTTTATTATCCTGAACTTCACCTTAATCTAAATTATACAAACCCAACTATCCAATTTG
       CAGAAATAATAGGACTTGAAGTGGAATTAGATTTAATATGTTTGGGTTGATAGGTTAAAC

MetLysPheSerThrIleLeuAlaAlaSerThrAlaLeuIleSer
301    AACTATCCAATATTATGAAATTCTCTACTATATTAGCCGCATCTACTGCTTTAATTTCC
       TTGATAGGTTATAATACTTTAAGAGATGATATAATCGGCGTAGATGACGAAATTAAAGG

309 SSP1,

361    ValValMetAlaAlaProValSerThrGluThrAspIleAspAspLeuProIleSerVal
       GTTGTTATGGCTGCTCCAGTTTCTACCGAAACTGACATCGACGATCTTCCAATTTCGGTT
       CAACAATACCGACGAGGTCAAAGATGGCTTTGACTGTAGCTGCTAGAAGGTTAAAGCCAA

421    ProGluGluAlaLeuIleGlyPheIleAspLeuThrGlyAspGluValSerLeuLeuPro
       CCAGAAGAAGCCTTGATTGGATTCATTGACTTAACCGGGGATGAAGTTTCCTTGTTGCCT
       GGTCTTCTTCGGAACTAACCTAAGTAACTGAATTGGCCCCTACTTCAAAGGAACAACGGA

481    ValAsnAsnGlyThrHisThrGlyIleLeuPheLeuAsnThrThrIleAlaGluAlaAla
       GTTAATAACGGAACCCACACTGGTATTCTATTCTTAAACACCACCATCGCTGAAGCTGCT
       CAATTATTGCCTTGGGTGTGACCATAAGATAAGAATTTGTGGTGGTAGCGACTTCGACGA

541    PheAlaAspLysAspAspLeuLysLysArgGluAlaAspAlaSerProTrpSerTrpIle
       TTCGCTGACAAGGATGATTTGAAGAAAAGAGAAGCCGATGCTTCCCCATGGAGTTGGATT
       AAGCGACTGTTCCTACTAAACTTCTTTTCTCTTCGGCTACGAAGGGGTACCTCAACCTAA

585 BSTXI NCO1,

601    ThrLeuArgProGlyGlnProIlePheLysArgGluAlaAsnAlaAspAlaAsnAlaGluAla
       ACTCTAAGACCTGGTCAACCAATCTTTAAAAGAGAAGCCAACGCTGACGCTAATGCTGAAGCA
       TGAGATTCTGGACCAGTTGGTTAGAAATTTTCTCTTCGGTTGCGACTGCGATTACGACTTCGT

607 TTH3I, 624 AHA3,
```

```
          SerProTrpSerTrpIleThrLeuArgProGlyGlnProIlePheLysArgGluAlaAsn
663       TCCCCATGGAGCTGGATTACTCTAAGACCTGGTCAACCGATCTTTAAGAGAGAGGCTAAT
          AGGGGTACCTCGACCTAATGAGATTCTGGACCAGTTGGCTAGAAATTCTCTCTCCGATTA

666 BSTXI, NCOI, 688 TTH3I

AlaAspAlaAsnAlaAspAlaSerProTrpSerTrpIleThrLeuArgProGlyGlnPro
723       GCTGATGCCAATGCAGATGCCTCCCCATGGAGCTGGATCACTCTAAGACCTGGTCAACCA
          CGACTACGGTTACGTCTACGGAGGGGTACCTCGACCTAGTGAGATTCTGGACCAGTTGGT

747 BSTXI, NCOI, 769 TTH3I

IlePheLysArgGluAlaAsnProGluAlaGluAlaAspAlaLysProSerAlaTrpSer
783       ATCTTTAAAAGAGAAGCCAACCCTGAGGCCGAGGCTGATGCCAAACCTAGTGCTTGGAGT
          TAGAAATTTTCTCTTCGGTTGGGACTCCGGCTCCGACTACGGTTTGGATCACGAACCTCA

786 AHA3, 804 MST2

TrpIleThrLeuArgProGlyGlnProIlePheOP
843       TGGATTACATTAAGACCTGGCCAACCAATTTTCTGAATTAGAAGGAAATTGACTTTTTGA
          ACCTAATGTAATTCTGGACCGGTTGGTTAAAAGACTTAATCTTCCTTTAACTGAAAAACT

860 BALI

903       CTCGTTTTCCAATGCGTCTATCTAATTTCTTCCAAAAGACAATACCCATCTTCCTTATAC
          GAGCAAAAGGTTACGCAGATAGATTAAAGAAGGTTTTCTGTTATGGGTAGAAGGAATATG

963       TTTTTTTATTTATCCAAACGAATTC
          AAAAAAATAAATAGGTTTGCTTAAG

982 ECORI
```

```
α-Factor Leader ---->< ----(Spacer) Prochymosin ----- pAB309,     LysAspPheLeuLysLysArgGluAlaAspAlaAspSerHisHisMetAlaGluIleThrArgIle
pAB312      AAGGATGATTTGAAGAAAAGAGAAGCCGATGCTGATTCCCATCATATGGCTGAGATCACCAGGATC
            TTCCTACTAAACTTCTTTTCTCTTCGGCTACGACTAAGGGTAGTATACCGACTCTAGTGGTCCTAG pAB313      LysAspPheLeuLysLysArgAlaGluIleThrArgIleProLeuTyrLysGly
            AAGGATGATTTGAAGAAAAGAGCTGAGATCACCAGGATCCCTCTGTACAAAGGC
            TTCCTACTAAACTTCTTTTCTCGACTCTAGTGGTCCTAGGGAGACATGTTTCCG pAB314      LysAspPheLeuLysLysArgAlaGluIleThrArgIleProLeuTyrLysGly
            AAGGATGATTTGAAGAAAAGAGGGCTGAGATCACCAGGATCCCTCTGTACAAAGGC
            TTCCTACTAAACTTCTTTTCTCCGCGACTCTAGTGGTCCTAGGGAGACATGTTTCCG
                              BssHII
``` pAB309 BamHI/SalI Insert in pUC18

```
  1 GGATCCCCAGCTTAGTTCATAGGTCCATTCTCTTAGCGCAACTACAGAGAACAGGGGCAC
    CCTAGGGGTCGAATCAAGTATCCAGGTAAGAGAATCGCGTTGATGTCTCTTGTCCCCGTG

1 BAMHI,

61 AAACAGGCAAAAAACGGGCACAACCTCAATGGAGTGATGCAACCTGCCTGGAGTAAATGA
    TTTGTCCGTTTTTTGCCCGTGTTGGAGTTACCTCACTACGTTGGACGGACCTCATTTACT

121 TGACACAAGGCAATTGACCCACGCATGTATCTATCTCATTTTCTTACACCTTCTATTACC
    ACTGTGTTCCGTTAACTGGGTGCGTACATAGATAGAGTAAAAGAATGTGGAAGATAATGG

181 TTCTGCTCTCTCTGATTTGGAAAAAGCTGAAAAAAAAGGTTGAAACCAGTTCCCTGAAAT
    AAGACGAGAGAGACTAAACCTTTTTCGACTTTTTTTCCAACTTTGGTCAAGGGACTTTA

236 XMNI,

241 TATTCCCCTACTTGACTAATAAGTATATAAAGACGGTAGGTATTGATTGTAATTCTGTAA
    ATAAGGGGATGAACTGATTATTCATATATTTCTGCCATCCATAACTAACATTAAGACATT

301 ATCTATTTCTTAAACTTCTTAAATTCTACTTTTATAGTTAGTCTTTTTTTTAGTTTTAAA
    TAGATAAAGAATTTGAAGAATTTAAGATGAAAATATCAATCAGAAAAAAAATCAAAATTT

355 AHA3,

MetLysPheSer
361 ACACCAAGAACTTAGTTTCGAATAAACACACATAAACAGATCTTCATTATGAAATTCTCT
    TGTGGTTCTTGAATCAAAGCTTATTTGTGTGTATTTGTCTAGAAGTAATACTTTAAGAGA

377 ASU2, 398 BGL2,

ThrIleLeuAlaAlaSerThrAlaLeuIleSerValValMetAlaAlaProValSerThr
421 ACTATATTAGCCGCATCTACTGCTTTAATTTCCGTTGTTATGGCTGCTCCAGTTTCTACC
    TGATATAATCGGCGTAGATGACGAAATTAAAGGCAACAATACCGACGAGGTCAAAGATGG

GluThrAspIleAspAspLeuProIleSerValProGluGluAlaLeuIleGlyPheIle
481 GAAACTGACATCGACGATCTTCCAATTTCGGTTCCAGAAGAAGCCTTGATTGGATTCATT
    CTTTGACTGTAGCTGCTAGAAGGTTAAAGCCAAGGTCTTCTTCGGAACTAACCTAAGTAA

AspLeuThrGlyAspGluValSerLeuLeuProValAsnAsnGlyThrHisThrGlyIle
541 GACTTAACCGGGGATGAAGTTTCCTTGTTGCCTGTTAATAACGGAACCCACACTGGTATT
    CTGAATTGGCCCCTACTTCAAAGGAACAACGGACAATTATTGCCTTGGGTGTGACCATAA

586 HGIE2,
```

```
       LeuPheLeuAsnThrThrIleAlaGluAlaAlaPheAlaAspLysAspAspLeuLysLys
601    CTATTCTTAAACACCACCATCGCTGAAGCTGCTTTCGCTGACAAGGATGATTTGAAGAAA
       GATAAGAATTTGTGGTGGTAGCGACTTCGACGAAAGCGACTGTTCCTACTAAACTTCTTT

ArgGluAlaAspAlaSerHisHisMetAlaGluIleThrArgIleProLeuTyrLysGly
661    AGAGAAGCCGATGCTTCCCATCATATGGCTGAGATCACCAGGATCCCTCTGTACAAAGGC
       TCTCTTCGGCTACGAAGGGTAGTATACCGACTCTAGTGGTCCTAGGGAGACATGTTTCCG

682 NDEI, 701 BAMHI,

LysSerLeuArgLysAlaLeuLysGluHisGlyLeuLeuGluAspPheLeuGlnLysGln
721    AAGTCTCTGAGGAAGGCGCTGAAGGAGCATGGGCTTCTGGAGGACTTCCTGCAGAAACAG
       TTCAGAGACTCCTTCCGCGACTTCCTCGTACCCGAAGACCTCCTGAAGGACGTCTTTGTC

769 PSTI,

GlnTyrGlyIleSerSerLysTyrSerGlyPheGlyGluValAlaSerValProLeuThr
781    CAGTATGGCATCAGCAGCAAGTACTCCGGCTTCGGGGAGGTGGCCAGCGTCCCCCTGACC
       GTCATACCGTAGTCGTCGTTCATGAGGCCGAAGCCCCTCCACCGGTCGCAGGGGGACTGG

800 SCAI, 821 BALI, 839 BSTXI,

AsnTyrLeuAspSerGlnTyrPheGlyLysIleTyrLeuGlyThrProProGlnGluPhe
841    AACTACCTGGACAGTCAGTACTTTGGGAAGATCTACCTCGGGACCCCGCCCCAGGAGTTC
       TTGATGGACCTGTCAGTCATGAAACCCTTCTAGATGGAGCCCTGGGGCGGGGTCCTCAAG

857 SCAI, 869 BGL2,

ThrValLeuPheAspThrGlySerSerAspPheTrpValProSerIleTyrCysLysSer
901    ACCGTGCTGTTTGACACTGGCTCCTCTGACTTCTGGGTACCCTCTATCTACTGCAAGAGC
       TGGCACGACAAACTGTGACCGAGGAGACTGAAGACCCATGGGAGATAGATGACGTTCTCG

936 KPNI,

AsnAlaCysLysAsnHisGlnArgPheAspProArgLysSerSerThrPheGlnAsnLeu
961    AATGCCTGCAAAAACCACCAGCGCTTCGACCCGAGAAAGTCGTCCACCTTCCAGAACCTG
       TTACGGACGTTTTTGGTGGTCGCGAAGCTGGGCTCTTTCAGCAGGTGGAAGGTCTTGGAC

GlyLysProLeuSerIleHisTyrGlyThrGlySerMetGlnGlyIleLeuGlyTyrAsp
1021   GGCAAGCCCCTGTCTATCCACTACGGGACAGGCAGCATGCAGGGCATCCTGGGCTATGAC
       CCGTTCGGGGACAGATAGGTGATGCCCTGTCCGTCGTACGTCCCGTAGGACCCGATACTG

1055 SPHI, 1078 TTH3I,

ThrValThrValSerAsnIleValAspIleGlnGlnThrValGlyLeuSerThrGlnGlu
1081   ACCGTCACTGTCTCCAACATTGTGGACATCCAGCAGACAGTAGGCCTGAGCACCCAGGAG
       TGGCAGTGACAGAGGTTGTAACACCTGTAGGTCGTCTGTCATCCGGACTCGTGGGTCCTC

1094 BSTXI, 1122 STUI,
```

```
           ProGlyAspValPheThrTyrAlaGluPheAspGlyIleLeuGlyMetAlaTyrProSer
1141  CCCGGGGACGTCTTCACCTATGCCGAATTCGACGGGATCCTGGGGATGGCCTACCCCTCG
      GGGCCCCTGCAGAAGTGGATACGGCTTAAGCTGCCCTAGGACCCCTACCGGATGGGGAGC
```

1141 SMAI, 1147 AAT2, 1165 ECORI, 1175 BAMHI,

```
           LeuAlaSerGluTyrSerIleProValPheAspAsnMetMetAsnArgHisLeuValAla
1201  CTCGCCTCAGAGTACTCGATACCCGTGTTTGACAACATGATGAACAGGCACCTGGTGGCC
      GAGCGGAGTCTCATGAGCTATGGGCACAAACTGTTGTACTACTTGTCCGTGGACCACCGG
```

1211 SCAI,

```
           GlnAspLeuPheSerValTyrMetAspArgAsnGlyGlnGluSerMetLeuThrLeuGly
1261  CAAGACCTGTTCTCGGTTTACATGGACAGGAATGGCCAGGAGAGCATGCTCACGCTGGGG
      GTTCTGGACAAGAGCCAAATGTACCTGTCCTTACCGGTCCTCTCGTACGAGTGCGACCCC
```

1293 BALI, 1304 SPHI,

```
           AlaIleAspProSerTyrTyrThrGlySerLeuHisTrpValProValThrValGlnGln
1321  GCCATCGACCCGTCCTACTACACAGGGTCCCTGCATTGGGTGCCCGTGACAGTGCAGCAG
      CGGTAGCTGGGCAGGATGATGTGTCCCAGGGACGTAACCCACGGGCACTGTCACGTCGTC
```

1379 SCAI,

```
           TyrTrpGlnPheThrValAspSerValThrIleSerGlyValValValAlaCysGluGly
1381  TACTGGCAGTTCACTGTGGACAGTGTCACCATCAGCGGTGTGGTTGTGGCCTGTGAGGGT
      ATGACCGTCAAGTGACACCTGTCACAGTGGTAGTCGCCACACCAACACCGGACACTCCCA
```

1399 TTH3I, 1408 HGIE2,

```
           GlyCysGlnAlaIleLeuAspThrGlyThrSerLysLeuValGlyProSerSerAspIle
1441  GGCTGTCAGGCCATCCTGGACACGGGCACCTCCAAGCTGGTCGGGCCCAGCAGCGACATC
      CCGACAGTCCGGTAGGACCTGTGCCCGTGGAGGTTCGACCAGCCCGGGTCGTCGCTGTAG
```

1483 APAI,

```
           LeuAsnIleGlnGlnAlaIleGlyAlaThrGlnAsnGlnTyrGlyGluPheAspIleAsp
1501  CTCAACATCCAGCAGGCCATTGGAGCCACACAGAACCAGTACGGTGAGTTTGACATCGAC
      GAGTTGTAGGTCGTCCGGTAACCTCGGTGTGTCTTGGTCATGCCACTCAAACTGTAGCTG
```

```
           CysAspAsnLeuSerTyrMetProThrValValPheGluIleAsnGlyLysMetTyrPro
1561  TGCGACAACCTGAGCTACATGCCCACTGTGGTCTTTGAGATCAATGGCAAAATGTACCCA
      ACGCTGTTGGACTCGATGTACGGGTGACACCAGAAACTCTAGTTACCGTTTTACATGGGT
```

```
           LeuThrProSerAlaTyrThrSerGlnAspGlnGlyPheCysThrSerGlyPheGlnSer
1621  CTGACCCCCTCCGCCTATACCAGCCAGGACCAGGGCTTCTGTACCAGTGGCTTCCAGAGT
      GACTGGGGGAGGCGGATATGGTCGGTCCTGGTCCCGAAGACATGGTCACCGAAGGTCTCA
```

```
          GluAsnHisSerGlnLysTrpIleLeuGlyAspValPheIleArgGluTyrTyrSerVal
1681      GAAAATCATTCCCAGAAATGGATCCTGGGGATGTTTTCATCCGAGAGTATTACAGCGTC
          CTTTTAGTAAGGGTCTTTACCTAGGACCCCCTACAAAAGTAGGCTCTCATAATGTCGCAG

1700 BAMHI,

PheAspArgAlaAsnAsnLeuValGlyLeuAlaLysAlaIleOP
1741      TTTGACAGGGCCAACAACCTCGTGGGGCTGGCCAAAGCCATCTGATCTCGACTTGGTTGA
          AAACTGTCCCGGTTGTTGGAGCACCCCGACCGGTTTCGGTAGACTAGAGCTGAACCAACT

1769 BALI,

1801      ACACGTTGCCAAGGCTTAAGTGAATTTACTTTAAAGTCTTGCATTTAAATAAATTTTCTT
          TGTGCAACGGTTCCGAATTCACTTAAATGAAATTTCAGAACGTAAATTTATTTAAAAGAA

1815 AFL2, 1830 AHA3, 1844 AHA3,

1861      TTTATAGCTTTATGACTTAGTTTCAATTTATATACTATTTTAATGACATTTTCGATTCAT
          AAATATCGAAATACTGAATCAAAGTTAAATATATGATAAAATTACTGTAAAAGCTAAGTA

1921      TGATTGAAAGCTTTGTGTTTTTTCTTGATGCGCTATTGCATTGTTCTTGTCTTTTTCGCC
          ACTAACTTTCGAAACACAAAAAAGAACTACGCGATAACGTAACAAGAACAGAAAAAGCGG

1928 HIND3,

1981      ACATGTAATATCTGTAGTAGATACCTGATACATTGTGGATGCTGAGTGAAATTTTAGTTA
          TGTACATTATAGACATCATCTATGGACTATGTAACACCTACGACTCACTTTAAAATCAAT

2041      ATAATGGAGGCGCTCTTAATAATTTTGGGGATATTGGCTTTTTTTTTTAAAGTTTACAAA
          TATTACCTCCGCGAGAATTATTAAAACCCCTATAACCGAAAAAAAAAATTTCAAATGTTT

2086 AHA3,

2101      TGAATTTTTTCCGCCAGGATAACGATTCTGAAGTTACTCTTAGCGTTCCTATCGGTACAG
          ACTTAAAAAAGGCGGTCCTATTGCTAAGACTTCAATGAGAATCGCAAGGATAGCCATGTC

2102 XMNI,

2161      CCATCAAATCATGCCTATAAATCATGCCTATATTTGCGTGCAGTCAGTATCATCTACATG
          GGTAGTTTAGTACGGATATTTAGTACGGATATAAACGCACGTCAGTCATAGTAGATGTAC

2221      AAAAAAACTCCCGCAATTTCTTATAGAATACGTTGAAAATTAAATGTACGCGCCAAGATA
          TTTTTTTGAGGGCGTTAAAGAATATCTTATGCAACTTTTAATTTACATGCGCGGTTCTAT

2281      AGATAACATATATCTAGCTAGATGCAGTAATATACACAGATTCCCGCGGACGTGGGAAGG
          TCTATTGTATATAGATCGATCTACGTCATTATATGTGTCTAAGGGCGCCTGCACCCTTCC

2324 SAC2,
```

2341 AAAAAATTAGATAACAAAATCTGAGTGATATGGAAATTCCGCTGTATAGCTCATATCTTT
     TTTTTTAATCTATTGTTTTAGACTCACTATACCTTTAAGGCGACATATCGAGTATAGAAA

2401 CCCTTCAACACCAGAAATGTAAAAATCTTGTTACGAAGGATCTTTTTGCTAATGTTTCTC
     GGGAAGTTGTGGTCTTTACATTTTTAGAACAATGCTTCCTAGAAAAACGATTACAAAGAG

2461 GCTCAATCCTCATTTCTTCCCTACGAAGAGTCAAATCTACTTGTTTTCTGCCGGTATCAA
     CGAGTTAGGAGTAAAGAAGGGATGCTTCTCAGTTTAGATGAACAAAAGACGGCCATAGTT

2521 GATCCATATCTTCTAGTTTCACCATCAAAGTCCAATTTCTAGTATACAGTTTATGTCCCA
     CTAGGTATAGAAGATCAAAGTGGTAGTTTCAGGTTAAAGATCATATGTCAAATACAGGGT

2562 SNAI,

2581 ACGTAACAGACAATCAAAATTGGAAAGGATAAGTATCCTTCAAAGAATGATTCTGCGCTG
     TGCATTGTCTGTTAGTTTTAACCTTTCCTATTCATAGGAAGTTTCTTACTAAGACGCGAC

2641 GCTCCTGAACCGCCTAATGGGAACAGAGAAGTCCAAAACGATGCTATAAGAACCAGAAAT
     CGAGGACTTGGCGGATTACCCTTGTCTCTTCAGGTTTTGCTACGATATTCTTGGTCTTTA

2701 AAAACGATAAAACCATACCAGGATCC
     TTTTGCTATTTTGGTATGGTCCTAGG

2721 BAMHI,

Primer #1: Spacer Deletion

5' GATTTGAAGAAAAGAGCTGAGATCACCAGG 3'

Primer #2: Spacer Deletion + BssHII Site

5' GATTTGAAGAA<u>GCGCG</u>CTGAGATCACCAGG 3'
            BssHII

```
         -840       -830       -820       -810       -800       -790
         GAATTCCTCA GTTTCAAGAT CTTTTAATGT CCAAAACCAT TTGAGCCGAT CTAAATACTT
         -780       -770       -760       -750       -740       -730
         CTGTGTTTTC ATTAATTTAT AAATTGTACT CTTTTAAGAC ATGGAAAGTA CCAACATCGG
         -720       -710       -700       -690       -680       -670
         TTGAAACAGT TTTTCATTTA CATATGGTTT ATTGGTTTTT CCAGTGAATG ATTATTTGTC
         -660       -650       -640       -630       -620       -610
         GTTACCCTTT CGTAAAACTT CAAACACGTT TTTAAGTATT GTTAGTTGC  TCTTTCGACA
         -600       -590       -580       -570       -560       -550
         TATATGATTA TCCCTGCGCG GCTAAAGTTA AAGATGCAAA AAACAGAAGA CAACTGAAGT
         -540       -530       -520       -510       -500       -490
         TAATTTACGT CAATTAAGTT TTCCAGGGTA ATGATGTTTT GGGCTTCCAC TAATTCAATA
         -480       -470       -460       -450       -440       -430
         AGTATGTCAT GAAATACGTT GTGAAGAGCA TCCAGAAATA ATGAAAAGAA ACAACGAAAC
         -420       -410       -400       -390       -380       -370
         TGGGTCGGCC TGTTGTTTCT TTTCTTTACC ACGTGATCTG CGGCATTTAC AGGAAGTCGC
         -360       -350       -340       -330       -320       -310
         GCGTTTTGCG CAGTTGTTGC AACGCAGCTA CGGCTAACAA AGCCTAGTGG AACTCGACTG
         -300       -290       -280       -270       -260       -250
         ATGTGTTAGG GCCTAAAACT GGTGGTGACA GCTGAAGTGA ACTATTCAAT CCAATCATGT
         -240       -230       -220       -210       -200       -190
         CATGGCTGTC ACAAAGACCT TGCGGACCGC ACGTACGAAC ACATACGTAT GCTAATATGT
         -180       -170       -160       -150       -140       -130
         GTTTTGATAG TACCCAGTGA TCGCAGACCT GCAATTTTTT TGTAGGTTTG GAAGAATATA
         -120       -110       -100        -90        -80        -70
         TAAAGGTTGC ACTCATTCAA GATAGTTTTT TTCTTGTGTG TCTATTCATT TTATTATTGT
          -60        -50        -40        -30        -20        -10
         TTGTTTAAAT GTTAAAAAAA CCAAGAACTT AGTTCAAAT  TAAATTCATC ACACAAACAA
           -1
         ACAAAACAAA ATG
```

FIG.18

```
           7         17          27          37          47          57
    TAAATTTAAC TCCTTAAGGT TACTTTAATG ATTTAGTTTT TATTATTAAT AATTCATGCT
          67         77          87          97         107         117
    CATGACATCT CATATACACG TTTATAAAAC TTAAATAGAT TGAAAATGTA TTAAAGATTC
         127        137         147         157         167         177
    CTCAGGGATT CGATTTTTTT GGAAGTTTTT GTTTTTTTTT CCTTGAGATG CTGTAGTATT
         187        197         207         217         227         237
    TGGGAACAAT TATACAATCG AAAGATATAT GCTTACATTC GACCGTTTTA GCCGTGATCA
         247        257         267         277         287         297
    TTATCCTATA GTAACATAAC CTGAAGTATA ACTGACACTA CTATCATCAA TACTTGTCAC
         307        317         327         337         347         357
    ATGAGAACTC TGTGAATAAT TAGGCCACTG AAATTTGATG CCTGAAGGAC CGGCATCACG
         367        377         387         397         407         417
    TATCTTCGAT AAAGCACTTA GTATCACACT AATTGGCTTT TCGCCGCATA TGGTGTTTCC
         427        437         447         457         467         477
    GGTGATTTCC AAGTATTGTT TCCAAGCATC GTACCTTTCA CCATTTGGAG TATCACTTAG
         487        497         507         517         527         537
    CGTTTTCATC GCATATCTGT CCATTATTTC AATGGATTGC CAAATGGGAA CTTGATGATG
         547        557         567         577         587         597
    TGAAAGTTTA CTCCTAGCAG TTAACATTTC CACTTCTGTT TCCTCTTTAA TGGCATTCAT
         607        617         627         637         647         657
    TCAACTCTTC CTTGCTTACC GACGTACCCG TATATTGGAA TCTGCGGCCC CAATGACAGA
         667        677         687         697         707         710
    AATCACTGCT TACAATGAAT AAATTGTTCG GATCCTTAAT GTACTCCGAC AAAATATTAC
         727        737         747         757         767         777
    CAATGCAACG ATCAACATCA ACGCTGTTAT GAGAAACCAT CATGGGAATT ACCTTCACCG
         787        797         807         817         827         837
    TATCTAAAGA AATTTCTCTC CATTTCAAAG TTTCCACCAA CATGGGAGC TGCATCTCTA
         847        857         867         877         887         897
    AGGAATGTTC AGCCATATCA GTGTCATGAT CCATTGGCTT AAACAGCTTC TTTCCGTTCT
         907        917         927         937         947         957
    CAGGATACTC CTTCTGTATT AATGTTTTAC ACAAGTCTGT ATCCACTTTC AGATTACCCA
         967        977         987         997        1007        1017
    AGGGCGTCTC TAGCTCACTG AATGCACTAA CTAAAATTTG GTTTTGAAA TAGATGTGAT
        1027       1037        1047        1057        1067        1077
    GCGACGGCCC CAAGATAAAT ATTCTCTTAA CATTACGGTT CAAATCCAAC GATGCGTACG
        1087       1097        1107        1117        1127        1137
    AGTAGGCCAT AGTGGGTCCA CAATACCTGT AACCGGCATG AGGACATATG ATAATTCTGG
        1147       1157        1167        1177        1187        1197
    CGTTGTGAAT TGGGCCTTTA AGGGTACTTT TGATCAAGTA TGTATGCGGT TGTTGAGATA
        1207       1217        1227        1237        1247        1257
    ATTCTTGGGC TCTATTGGAA TACCATGAGC CTGCATGTGT TGCTGGACGT ATTGACATGT
        1267       1277        1287        1297        1307        1317
    TTGAAAAATT CTATTCTTTG CACTGTAGTC CACCTAAGCC ACCGACTAGG ACCACTTCAC
        1322
    TTAAG
```

FIG. 21

<u>Sac I</u>

5' CCC.TTA.GTT.TCA.AAT.TAA.AGA.GCT.CAT.CAC 3'

3' TCT.CGA.GTA.GTG.TGT.TTG.TTT.GTT.TTG.TTT 5'

Klenow DNA-polymerase
dNTP's

<u>Dde I</u>　　　　　　<u>Sac I</u>

5' CCC.TTA.GTT.TCA.AAT.TAA.AGA.GCT.CAT.CAC.ACA.AAC.AAA.CAA.AAC.AAA 3'
3' GGG.AAT.CAA.AGT.TTA.ATT.TCT.CGA.GTA.GTG.TGT.TTG.TTT.GTT.TTG.TTT 5'

Dde I
<u>Sac I</u>

5' TTA.GTT.TCA.AAT.TAA.AGA.GCT.CAT.CAC.ACA.AAC.AAA.CAA.AAC.AAA 3'
3' CAA.AGT.TTA.ATT.TCT.CGA.GTA.GTG.TGT.TTG.TTT.GTT.TTG.TTT 5'

Sac I

T$_4$ DNA-polymerase, dNTP's

T$_4$ DNA ligase

5' TTA.GTT.TCA.AAT.TAA.AGC.ATC.ACA.CAA.ACA.AAC.AAA.ACA.AA 3'
3' CAA.AGT.TTA.ATT.TCG.TAG.TGT.GTT.TGT.TTG.TTT.TGT.TT 5'

KLUYVEROMYCES AS A HOST STRAIN

CROSS REFERENCE TO RELATED APPLICATIONS

This application is a continuation-in-part of U.S. Application Ser. No. 572,414, filed Jan. 19, 1984, now U.S. Pat. No. 4859596, which disclosure is incorporated herein by reference.

INTRODUCTION

1. Technical Field

This invention relates to methods for preparing and using Kluyveromyces for the production of polypeptides of interest which preferentially are secreted into the growth medium. The invention is exemplified by sequences useful in the production of chymosin and precursors thereof in Kluyveromyces.

1. Background

The bright promise of production of peptides in microorganisms has been tarnished by a number of factors. In many instances, where the peptide has been produced and retained in the cytoplasm, inclusion bodies have resulted requiring denaturation and renaturation of the protein, frequently with only partial or little success. In other instances, the peptide has been subjected to substantial degradation, so that not only are yields low, but also complicated mixtures are obtained which are difficult to separate. As a potential solution to these difficulties, the possibility of secretion of the desired peptide into the nutrient medium has been investigated. Secretion has met with limited success, since not all proteins have been found to be capable of secretion in the hosts which have been employed. Even when secreted, the processing of the peptide may result in a product which differs from the composition and/or conformation of the desired peptide. There is therefore, substantial interest in being able to develop systems for the efficient and economic production of active peptides under conditions which allow for the use of the peptides in a wide variety of environments, both in vitro and in vivo.

RELEVANT LITERATURE

European Patent Application No. 0,096,430, the European analog of the subject parent application and the references cited therein. The leader sequence of amyloglucosidase for Aspergillus is described in Boyle et al., *EMBO J.* (1984) 3:1581-1585 and Innis et al., *Science* 1985) 228:21-26. Lactase promoters are described in Bruenig et al., *Nucleic Acids Res.* (1984) 12:2327-2341. See also European Patent Application 0,123,544. The use of signal peptides associated with mating-type alpha factor and of the enzymes invertase and acid phosphatase to direct the secretion of heterologous proteins in Saccharomyces has been described by Singh (European Patent Application 84 302723.6) and by Smith et al. (*Science* (1985) 229:1219).

Production of preprochymosin, prochymosin and chymosin in Saccharomyces has been studied by Mellor et al., *Gene* (1983) 24:1-14. When prochymosin is made intracellularly in Saccharomyces, only a low percentage of the prochymosin obtained is activatable. See Moir et al. in *Developments in Industrial Biology* (1985) 26:75-85; Mellor et al., *Gene* (1983) 24:1-14; Kingsman et al. in *Biotechnology and Genetic Engineering Reviews* Vol. 3 (1985) pp. 376-418. The aggregated prochymosin produced by Saccharomyces required complicated methods of denaturation and renaturation to solubilize the prochymosin. See WO 83/04418 and EP-A-114506.

SUMMARY OF THE INVENTION

Peptide production systems are provided comprising Kluyveromyces host strains, expression cassettes which include efficient transcriptional initiation and termination regions for use in Kluyveromyces and a gene, optionally containing a signal sequence for secretion, under the transcriptional and translational regulation of the regulatory regions. The cassettes are introduced into the Kluyveromyces host strain under conditions whereby the resulting transformants stably maintain the expression cassettes. Naturally occurring DNA and synthetic genes may be employed for the production of peptides of interest.

BRIEF DESCRIPTION OF THE FIGURES

FIG. 1 is a flow diagram of the preparation of plasmids pGB 122, 123, 124 and 131;

FIG. 3 is a flow diagram of the preparation of plasmids pGB 161, 162, 163 and 164;

FIG. 5 is a description of the synthesized nucleotide signal sequence adapted from the amyloglucosidase signal sequence;

FIG. 6 is a description of a synthetic signal sequence;

FIG. 8 is the sequence of the entire BamHI insert from pDM100PC comprising the fusion peptide of the α-factor of *S. cerevisiae* and prochymosin and transcriptional regulatory regions;

FIG. 10 is the sequence of a set of nucleotides used as probes for the *K. lactis* α-factor peptide;

FIG. 11 is the sequence of a 1kbp *K. lactis* fragment which includes the α-factor peptide;

FIG. 13 is the sequence around the junction between the *S. cerevisiae* GAPDH regulatory regions and the prochymosin structural gene;

FIG. 14 is the sequence of the BamHI/SalI insert of pAB309;

FIG. 15 represents the sequences of the primers for mutagenesis of *K. lactis* α-factor leader DNA;

FIG. 17 is a nucleotide sequence of the 5'-non-coding region of the insert in pF2 1-33;

FIG. 18 is a partial nucleotide sequence of the coding region of the GAPDH gene;

FIG. 21 is a description of the preparation of a synthetic oligomer as an adapter between the GAPDH promoters and the initiation codon of the structural gene;

DESCRIPTION OF THE SPECIFIC EMBODIMENTS

Figure 2:
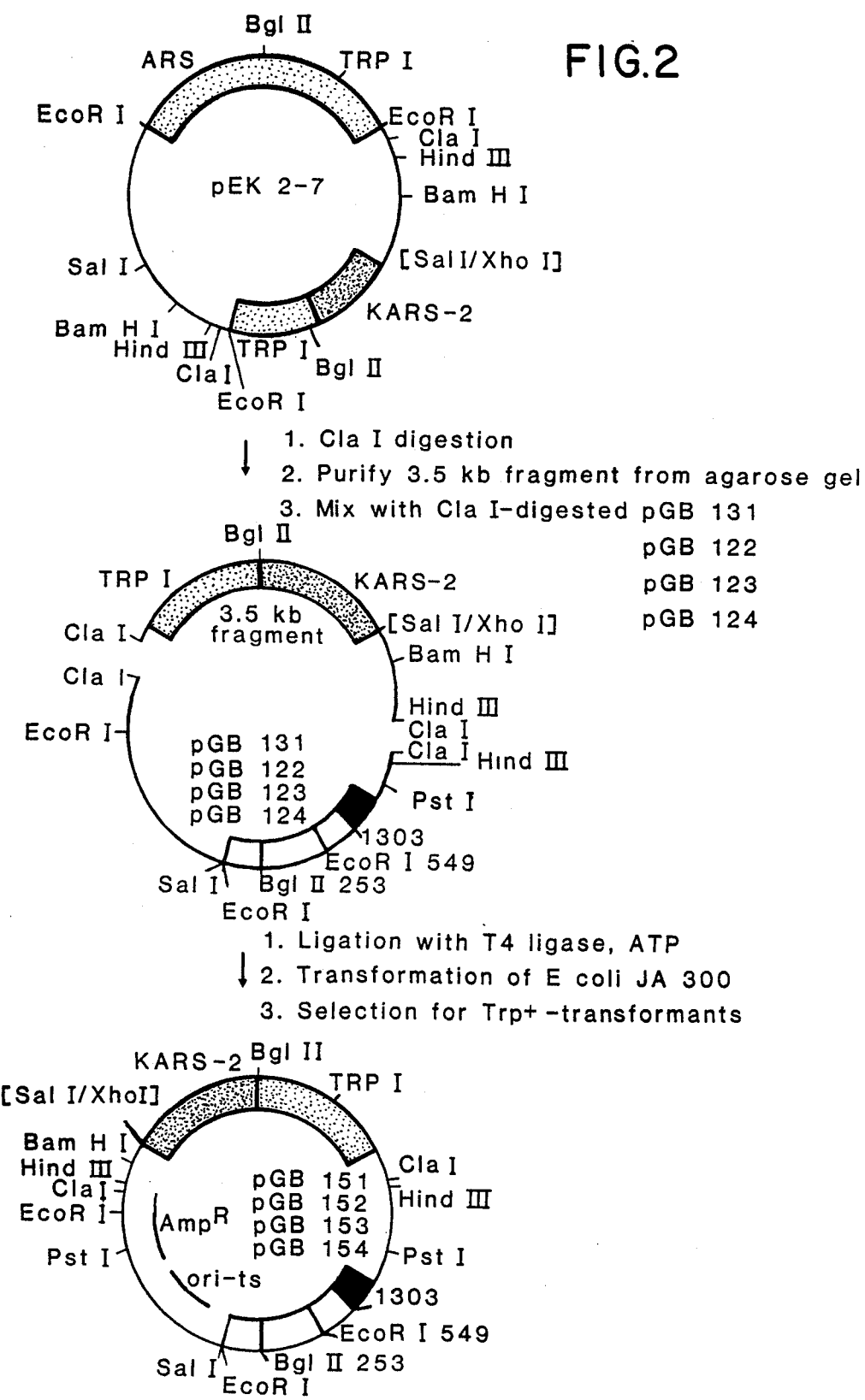
FIG. 2 is a flow diagram of the preparation of plasmids pGB 151, 152, 153 and 154.

In accordance with the subject invention, expression cassettes are provided which allow for the efficient and economic production of polypeptides by Kluyveromyces yeast cells. The expression cassettes have transcriptional and translational regulatory sequences functional in a Kluyveromyces host cell and an open reading frame coding for a peptide of interest under the transcriptional and translational control of the regulatory regions. The open reading frame also may include a leader sequence recognized by the Kluyveromyces host which provides for secretion of the polypeptide into the growth medium. The Kluyveromyces cells used may be either laboratory or industrial strains.

The expression cassette will include in the 5'-3' direction of transcription, a transcriptional and translational initiation regulatory region, an open reading frame encoding a peptide of interest, desirably having a signal sequence for secretion recognized by Kluyveromyces, and a translational termination region. The expression cassette will further comprise a transcriptional termination regulatory region. The initiation and termination regulatory regions are functional in Kluyveromyces and provide for efficient expression of the peptide of interest without undesirable effects on the viability and proliferation of the Kluyveromyces host.

The transcriptional and translational initiation regulatory region may be homologous or heterologous to Kluyveromyces. Of particular interest are transcriptional initiation regions from genes which are present in Kluyveromyces or other yeast species, such as Saccharomyces, for example, cerevisiae, Schizosaccharomyces, Candida, etc., or other fungi, for example, filamentous fungi such as Aspergillus, Neurospora, Penicillium, etc. The transcriptional initiation regulatory regions may be obtained for example from genes in the glycolytic pathway, such as alcohol dehydrogenase, glyceraldehyde-3-phosphate dehydrogenase, phosphoglucoisomerase, phosphoglycerate kinase, etc., or regulatable genes such as acid phosphatase, lactase, glucoamylase, etc.

Any one of a number of regulatory sequences may be preferred in a particular situation, depending upon whether constitutive or induced transcription is desired, the particular efficiency of the promoter in conjuction with the open reading frame of interest, the ability to join a strong promoter with a control region from a different promoter which allows for inducible transcription, ease of construction, and the like. These regulatory regions find ample precedent in the literature. See, for example, EPA 164,556, incorporated herein by reference.

Secretion of heterologous proteins in genetically modified microorganisms is generally accomplished by one of two methods. In the first, the leader sequence is homologous to the protein; in the second, the leader sequence is homologous to the host organism. Other alternatives of particular interest in the present invention for secretion of heterologous protein in Kluyveromyces include the use of a synthetic leader sequence or a leader sequence heterologous to both Kluyveromyces and the peptide of interest. Thus, the open reading frame usually will include a wild-type or mutated gene, where the signal sequence is normally associated with the remainder of the coding sequence, a hybrid or chimeric open reading frame, where the signal sequence is normally not associated with the remaining portion of the open reading frame, or a synthetic sequence, where the signal sequence and the remainder of the open reading frame are synthesized to provide for preferred codons, convenient restriction sites, novel amino acid sequences, and the like, or combinations thereof. Signal sequences which may be employed may be obtained from genes, such as alpha-factor, invertase, amyloglucosidase, native or wild type signal sequences present in structural genes and recognized by Kluyveromyces. Saccharomyces, other fungi, e.g. Neurospora, Aspergillus, and other eukaryotes.

Of particular interest is the use of a signal sequence which provides for secretion of the peptide of interest into the nutrient medium, rather than into the periplasmic space. For the most part, the signal sequence will be the 5'-terminus of the open reading frame. However, in some situations, it may be desirable to have the signal sequence internal to the open reading frame. For use of internal signal sequences for secretion see U.S. Pat. No. 4,338,397 and Perara and Lingappa, *J. Cell Biology* (1985) 101:2292-2301. Genes into which the open reading frame of interest may be inserted include highly expressed constitutive genes, for example, genes encoding enzymes of the glycolytic pathway, or highly expressed regulatable genes such as lactase, amyloglucosidase, or the like.

For optimal gene expression, the nucleotide sequences surrounding the translational initiation codon ATG have been found to be important in yeast cells and in animal cells. For example, M. Kozak (*Microbiol. Revs.* (1983) 47:1-45) has studied extensively the effect of these regions on the expression of insulin in COS cells. Similarly, specific nucleotides are found more frequently in highly expressed yeast proteins than others indicating the important effect of these nucleotides on the level of expression of these genes.

For optimal gene expression of exogenous genes it will be important to modify the nucleotide sequences surrounding the initiation codon ATG. This can be done by site-directed mutagenesis or by fusing the exogenous gene in frame to an endogenous Kluyveromyces gene, preferably a highly expressed gene, such as the lactase gene.

Normally, it will be desirable to provide that the signal leader is cleaved from the peptide of interest during the secretory process, rather than subsequent to the secretory process, although either procedure may find use. Usually, the processing signal employed will be the processing signal naturally occurring with the signal sequence or a processing signal which has been modified from the naturally occurring one, which is still effective for providing for a peptide signal resulting in hydrolytic cleavage of the signal peptide and processing signal peptide from the peptide of interest. Various processing signals have been sequenced and defined, such as α-factor (see for example U.S. Patent No. 4,546,082, which is incorporated herein by reference), amyloglucosidase, α-amylase, etc. In some instances, other peptidase-recognized sequences may be employed which may require subsequent cleavage for isolation of the desired peptide. These sequences include dibasic peptides, e.g. KR, (D)$_4$K, and EA, which are cleaved by KEX2, bovine enterokinase, and a yeast membrane peptidase, respectively.

The peptide of interest may be native to the host or heterologous, being derived from prokaryotic or eukaryotic sources, which eukaryotic sources may involve fungi, protists, vertebrates, non-vertebrates, and the like. The peptide products may include enzymes, such as lactase, α-amylase, β-amylase, amyloglucosidase, chymosin, etc., mammalian peptides, such as hormones, interleukins, cytokines, cachexin, growth factors, e.g. platelet derived, epidermal, skeletal, etc., growth hormone, follicle stimulating hormone, interferons (α-β-, and γ-), blood factors such as factor V, VI, VII, VIII (vW or c) IX, X, XI or XII, plasminogen activator, (tissue or urinary), serum albumin, colony growth factor (e.g. GM), erythropoietin, thaumatin, insulin, etc.

These structural genes may be obtained in a variety of ways. Where the amino acid sequence is known, the structural gene may be synthesized in whole or in part, particularly where it is desirable to provide yeast-preferred codons. Thus, all or a portion of the open reading frame may be synthesized using codons preferred by Kluyveromyces. Preferred codons may be determined by those codons which are found in the proteins produced in greatest amount by the Kluyveromyces host e.g. glycolytic enzymes. Methods for synthesizing sequences and bringing the sequences together are well established in the literature. Where a portion of the open reading frame is synthesized, and a portion is derived from natural sources, the synthesized portion may serve as a bridge between two naturally occurring portions, or may provide a 3'- terminus or a 5'-terminus. Particularly where the signal sequence and the open reading frame encoding the peptide are derived from different genes, synthetic adaptors commonly will be employed. In other instances, linkers may be employed, where the various fragments may be inserted at different restriction sites or substituted for a sequence in the linker.

For the most part, some or all of the open reading frame will be from a natural source. Methods for identifying sequences of interest have found extensive exemplification in the literature, although in individual situations, different degrees of difficulty may be encountered. Various techniques involve the use of probes, where at least a portion of the naturally occurring amino acid sequence is known, where genomic or cDNA libraries may be searched for complementary sequences. Alternatively, differential transcription can be detected when the gene of interest can be induced or when cells are from the same host but of different differentiation, by comparing the messenger RNA's produced. Other techniques have also been exemplified.

The termination region may be derived from the 3'-region of the gene from which the initiation region was obtained or from a different gene. A large number of termination regions are known and have been found to be satisfactory in a variety of hosts from the same and different genera and species. The termination region is usually selected more as a matter of convenience rather than because of any particular property. Preferably, the termination region will be derived from a yeast gene, particularly Saccharomyces or Kluyveromyces.

In developing the expression cassette, the various fragments comprising the regulatory regions and open reading frame may be subjected to different processing conditions, such as ligation, restriction, resection, in vitro mutagenesis, primer repair, use of linkers and adaptors, and the like. Thus, nucleotide transitions, transversions, insertions, deletions, or the like, may be performed on the DNA which is employed in the regulatory regions and/or open reading frame.

During the construction of the expression cassette, the various fragments of the DNA will usually be cloned in an appropriate cloning vector, which allows for expansion of the DNA, modification of the DNA or manipulation by joining or removing of the sequences, linkers, or the like. Normally, the vectors will be capable of replication in at least a relatively high copy number in *E. coli*. A number of vectors are readily available for cloning, including such vectors as pBR322, pACYC184, pUC7-19, M13, Charon 4A, and the like.

The cloning vectors are characterized by having an efficient replication system functional in *E. coli*. Also, the cloning vector will have at least one unique restriction site, usually a plurality of unique restriction sites and may also include multiple restriction sites, particularly two of the same restriction sites for substitution. In addition, the cloning vector will have one or more markers which provide for selection for transformants. The markers will normally provide for resistance to cytotoxic agents such as antibiotics, heavy metals, toxins or the like, complementation of an auxotrophic host, or immunity to a phage. By appropriate restriction of the vector and cassette, and, as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

In some instances a shuttle vector will be employed where the vector is capable of replication in different hosts requiring different replication systems. This may or may not require additional markers which are functional in the two hosts. Where such markers are required, these can be included in the vector, where the plasmid containing the cassette, the two replication systems, and the marker(s) may be transferred from one host to another, as required. In the present situation, the second replication system would be a replication system functional in Kluyveromyces. The replication systems which may be used may be derived from plasmids, viruses, or the chromosome of Kluyveromyces or other species, particularly one associated with Kluyveromyces, such as Saccharomyces. Thus, replication systems include the replication system of the 2 micron plasmid found in Saccharomyces and an autonomously replicating sequence (ARS) gene, for example when used in conjunction with a centromere sequence, or the like. If desired, regions of homology may be provided to encourage integration of the expression cassette into the genome of the Kluyveromyces host.

Of particular interest in the constructs of the subject invention is a sequence derived from Kluyveromyces DNA chromosomes referred to as KARS, which provide for high transformation frequency. The KARS gene may be obtained by screening a library of Kluyveromyces DNA fragments for enhanced transformation efficiency. In this manner, fragments can be obtained which contain KARS sequences, which fragments can be further modified by restriction, resection, or primer repair, to provide a fragment of approximately 200 bp and not more than about 5000 bp, more usually from about 200 bp to 2000 bp which provides for enhanced transformation efficiency. The presence of the KARS gene can provide transformation of *K. lactis* auxotrophic species to prototophy at a frequency of at least about $10^3$ per microgram of DNA, usually at a frequency of $10^4$ per microgram of DNA or higher.

The manner of transformation of *E. coli* with the various DNA constructs (plasmids and viruses) for cloning is not critical to this invention. Conjugation, transduction, transfection or transformation, e.g. calcium phosphate mediated transformation, may be employed. By contrast, for yeast, for the most part the prior art has relied on transformation of protoplasts employing combinations of calcium and polyethylene glycol of from about 2000 to 8000, usually 4000 to 7000 daltons.

An alternative method of transformation involves growing Kluyveromyces in a standard yeast nutrient medium to a density of 1 to 25, desirably 4 to 10 $OD_{610}$. The Kluyveromyces cells are then harvested, washed and pretreated with chaotropic ions particularly the alkali metal ions, lithium, cesium, or rubidium particularly as the chloride or sulfate, more particularly the lithium salts, at concentrations of about 2 mM to 1 M, preferably about 0.1 M. After incubating the cells in the presence of polyethylene glycol of 2000 to 6000 daltons, preferably 4000, for from about 5 to 120 min. preferably about 60 min. with the chaotropic ion(s), the cells are then incubated with DNA for a short period of time at a moderate temperature, generally from about 20° C. to 35° C., for about 5 min. to 60 min. Desirably, polyethylene glycol is added at a concentration to about 25 to 50%, where the entire medium may be diluted by adding an equal volume of a polyethylene glycol concentrate to result in the desired final concentration. The polyethylene glycol will be of from about 2000 to 8000 daltons, preferably about 4000 to 7000 daltons. Incubation will generally be for a relatively short time, generally from about 5 to 60 min. after the second addition of the polyethylene glycol. Desirably, the incubation medium is subjected to a heat treatment of from about 1 to 10 min. at about 35° C. to 45° C., preferably about 42° C.

For selection, any useful marker may be used, although the number of markers useful with Kluyveromyces is narrower than the markers used for Saccharomyces. Desirably, resistance to kanamycin and the aminoglycoside G418 are of interest, as well as complementation of a gene in the tryptophan metabolic pathway, particulary TRP1 or the lactase gene, particularly LAC4.

Although a marker for selection is highly desirable for convenience, other proceduress for screening transformed cells have been described. See for example G. Reipen et al., *Current Genetics* (1982) 189–193. Besides the use of an indicator enzyme such as beta-lactamase, transformed cells may be screened by the specific products they make. In the case of chymosin, for example, synthesis of the product may be determined by an immunological or an enzymatic method.

The vector used may be capable of extra chromosomal maintenance in Kluyveromyces or result in integration into the Kluyveromyces gene. It has been found that the 2 micron plasmid replication system from Saccharomyces provides for extrachromosonal maintenance in Kluyveromyces. In addition, one may use a combination of a centromere, such as the Saccharomyces CEN3 and a high transformation frequency sequence, such as ARS or KARS. If selective maintenance is provided, such as complementation or resistance to an antibiotic to which Kluyveromyces is susceptible, the ARS-like sequences will usually suffice for extrachromosomal maintenance.

For large scale fermentation even a small loss of plasmid stability will greatly effect the final yield of the desired protein. To increase the stability of recombinant molecules in host cells, for example Kluyveromyces, integration of the recombinant molecules into the host chromosome may be used.

Where integration is desired, it will usually be desirable to have a sequence homologous to a sequence of the chromosome of the host, so that homologous recombination may occur. It is understood, that random integration also occurs, so that the homologous sequence is optional. Where an homologous sequence is employed, the homologous sequence will usually be at least about 200 bp and may be 1000 bp or more. In addition, where integration is involved, one may wish to have amplification of the structural gene. Amplification has been achieved by providing for a gene in tandem with the desired structural gene, which provides for selective advantage for the host in a selective medium. Thus, the genes expressing dihydrofolate reductase, metallothioneins, thymidine kinase, etc., have proven useful in a variety of hosts to provide for amplification, where the gene provides protection from a toxin, such as methotrexate, heavy metals, such as copper and mercury, and the like.

Vectors of interest providing for stable replication include KARS vectors originating from *K. lactis*, e.g. pKARS12 and pKARS2, which plasmids comprise a *K. lactis* DNA fragment containing the KARS12 or KARS2 sequence in the *S. cerevisiae* plasmid YRp7. A vector employed for integration is illustrated by pL4, a hybrid plasmid of the ARS1 carrying plasmid YRp7 and *K. lactis* XhoI DNA fragment carrying the LAC4 gene.

Plasmids of particular interest include plasmids having the 2 micron plasmid replication system, the LAC4 gene, the Tn601 and Tn5 kanamycin resistance gene, which also provides resistance to the antibiotic G418 in Kluyveromyces (Jimenez and Davis, *Nature* (1980) 287:869,871). This plasmid provides for autonomous replication in Kluyveromyces and can be selected for by resistance to G418 on regeneration plates containing glucose, sorbitol, and 0.2 μg/ml G418, while avoiding elevated concentrations of KCl, which interferes with the sensitivity of Kluyveromyces to G418. Preferred plasmids include the TRP1 gene, particularly from *S. cerevisiae*, the LAC4 gene, particularly *K. lactis*, $Kan^R$ gene providing for resistance against antibiotic G418 from Tn5, or the like.

The subject vectors and constructs are introduced into an appropriate host for cloning and expression of the desired structural genes. After transformation, colonies will normally appear on regeneration medium within about 5 to 6 days. Where an antibiotic is employed for selection, the colonies should be screened to ensure the absence of spontaneous mutation to a resistant strain. Employing the plasmids and the methods of the subject invention, about 5% of resistant colonies were found to contain the plasmid construct providing for at least about 4 transformants per μg of plasmid DNA. Where selection was based on the presence of the LAC4 gene, using plates containing lactose as the sole carbon source and 0.6M KCl as an osmotic stabilizer, all of the surviving colonies were found to be transformants and not spontaneous revertants. About 20 transformants were obtained after about 4 to 5 days of incubation at moderate temperature, e.g. 30° C.

As a host organism, Kluyveromyces is especially suitable for the production of heterologous proteins, in particular for the production and extraction of the enzyme chymosin and its precursors preprochymosin, pseudochymosin and prochymosin. Although other organisms such as Saccharomyces produce prochymosin in reasonable amounts, the produced prochymosin cannot be extracted in an active or activatable form. We have surprisingly found that more than 90% of the total amount of the prochymosin produced by Kluyveromyces can be extracted in an active form with very simple standard techniques.

Any of the many Kluyveromyces species may be employed. Either laboratory or industrial, preferably industrial, strains may be used. By industrial species is intended, Kluyveromyces strains from organisms which may be isolated from natural sources or may be available from depositories or other sources or obtained by modification, e.g. mutation, of such strains. The industrial strains are characterized by being resistant to genetic exchange, being protrotophic or made protrotophic by a single gene being introduced into the host strain, and are usually selected for improved production of peptides. Among the Kluyveromyces species which may find use are *K. lactis, K. fragilis, K. bulgaricus, K. thermotolerans, K. marxianus*, etc. It should be further noted that the Kluyveromyces organisms are on the GRAS (Generally Recognized As Safe) list. Their use for production of products to be used in vivo or to be ingested normally will not require special governmental review and approval.

Both wild type and mutant Kluyveromyces, particularly *Kluyveromyces lactis* or *Kluyveromyces fragilis* may be employed as hosts. Hosts of particular interest include *K. lactis* SD11 lac4 trp1 and *K. lactis* SD69 lac4. These strains, derived from the wild-type CBS2360, were deposited under rule 28, resp. 28A of the European Patent Convention with Centraal Bureau Voor Schimmelcultures, Oosterstraat 1, 3742 SK Baarn, Netherlands, under numbers CBS8092 and CBS8093, respectively, on May 19, 1982.

For maintaining selective pressure on the transformants for maintenance of the plasmids, selective media may be used such as a yeast nitrogen-based medium, 2% lactose instead of glucose for *K. lactis* SD69 lac4 (PTY75-LAC4) and for *K. lactis* SD69 lac4 (pL4) and a yeast nitrogen-based medium (Difco) plus 2% glucose for *K. lactis* SD11 lac4 trp1 (pKARS12). Similarly, strains containing plasmids conferring antibiotic resistance, for example against gentamycin 418, may be cultivated in a medium containing said antibiotic.

Where the hybrid plasmids are employed for large scale production of the desired protein, it would generally be useful to remove at least substantially all of the bacterial DNA sequences from the hybrid plasmids.

Depending upon the nature of the structural gene of interest, the expression product may remain in the cytoplasm of the host cell or be secreted. It has been found that not only the proteins that remain in the cell but also those that are secreted are soluble. Where the expression product is to remain in the host cell, it may generally be desirable to have an inducible transcription initiation region, so that until the transformant has reached a high density, there is little or no expression of the desired product. After sufficient time for the expression product to form, the cells may be isolated by conventional means, e.g. centrifugation, lysed and the product of interest isolated. Depending upon the nature and use of the product, the lysate may be subjected to various purification methods, such as chromatography, electrophoresis, solvent extraction, crystallization, or the like. The degree of purity may vary from about 50%, to 90% or higher, up to essential purity.

Alternatively, the expression product may be secreted into the culture medium, and produced on a continuous basis, where the medium is partially withdrawn, the desired product extracted, e.g., by affinity chromatography, or the like, and the spent medium discarded or recirculated by restoring essential components. When the product is to be secreted, normally a constitutive transcriptional initiation region will be employed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following examples are offered by way of illustration and not by limitation.

EXPERIMENTAL

Example 1

Recombinant plasmid PTY75-LAC4

0.5 μg of the plasmid pK16 described by R. Dickson, (*Gene* (1980) 10:347–356) and 0.5 μg of the plasmid PTY75 described by C.P. Hollenberg et al. (*Gene* (1976) 1:33–47) were digested with the restriction enzyme SalI. The two digests were mixed and after inactivation of the restriction enzyme the solution was incubated with T4-ligase, yielding a solution with recombinant DNA.

This ligated mixture was used to transform the *E. coli* strain DG75 (hsdS1leu-6 ara-14 galK2 xyl-5 15 mt-1 rpsL20 thi-1 supE44-λ-lacΔz 39) according to R. C. Dickson et al., *Cell* (1978) 15:123–130, resulting in kanamycin resistance (Kan$^R$). Kan$^R$ colonies were further selected on supplemented minimal plates, containing lactose as the sole carbon source, for the formation of lac+ colonies. The plasmid PTY75-LAC4 was isolated from one of the selected Kan$^R$ lac+ transformants, using the method according to L. Katz et al., *J. Bacteriol.* (1973) 114:577–591.

Example 2

Recombinant pKARS plasmids

5 μg of plasmid YRp7 (Struhl et al., *Proc. Natl. Acad. Sci., USA* (1979) 76:1035–39) was digested with restriction enzyme SalI. 14 μg of DNA from the wild strain *K. lactis* CBS2360 was digested with enzyme XhoI. The fragments of the plasmid and the *K. lactis* DNA were mixed in a molar ratio of 1:3. After inactivation of the restriction enzymes the solution was brought to a DNA concentration of 25 μg/ml and incubated with T4-ligase (Boehringer) under standard conditions.

Transformation of E. coli DG75 with the ligated mixture under the usual conditions yielded a mixture of $4.5 \times 10^5$ Amp$^R$ transformants, $9 \times 10^3$ of which contained K. lactis inserts, as can be deduced from their sensitivity to tetracycline. The proportion of tetracycline-sensitive cells can be increased to 85% by cycloserine treatment. See F. Bolivar and K. Bachman, Methods in Enzymology (1979) 68:245-267. Fourteen different plasmids were isolated according to the method of Katz et al. (see Example 1). These plasmids are referred to as pKARS 1-14. All were capable of transforming K. lactis SD11 lac4 trp1 strain to Trp+ phenotype with a frequency of $3 \times 10^4$ per microgram of DNA, but plasmid pKARS2 appeared to be more convenient in further processing.

The recombinant plasmids obtained could also be transferred to E. coli JA221 (Δtrp E5, leu B6, lac y, rec A, hsdM+, hsdR−).

Example 3

Recombinant plasmid pL4

A mixture of YRp7 and K. lactis DNA fragments was prepared as described in Example 2. E. coli DG75 strain was transformed with the ligated mixture and subsequently plated on M9 minimal agar, which medium contained lactose as the sole carbon source, to which leucine was also added. Lac+ colonies appeared after 8 days at 30° C. Plasmid pL4 was isolated from one of these Lac+ colonies using the method of Katz et al. (see Example 1).

Example 4

Kluyveromyces lactis SD69 lac4 transformed to G418$^R$ Lac+ with plasmid PTY75-LAC4

Cells of the Kluyveromyces lactis mutant SD69 lac4 were suspended in a growth medium (pH 6.8) containing 1% yeast extract, 2% peptone and 2% glucose. Growth was continued until the exponential phase (3-$5 \times 10^7$ cells per ml) had been reached.

The yeast cells were collected by centrifugation, washed with water and resuspended in a solution (pH 8.0) containing 1.2 M sorbitol, 25 mM EDTA and 0.2 M fresh mercaptoethanol. After incubation for 10 min. at 30° C. the cells were centrifuged, washed two times with a 1.2 M sorbitol solution and resuspended in 20 ml of a solution (pH 5.8) containing 1.2 M sorbitol, 10 mM EDTA, 0.1 M sodium citrate and 10 mg helicase.

Protoplasts were formed and after 15 to 20 minutes they were centrifuged, washed three times with 1.2 M sorbitol and resuspended to a concentration of about $5 \times 10^{10}$ cells per ml in 0.1 ml of a solution containing 10 mM CaCl$_2$ and 1.2 M sorbitol.

10 μg of PTY75-LAC4 was added and the mixture was incubated for 15 min. at 25° C. Thereafter 0.5 ml of a solution (pH 7.5) containing 10 mM Tris, 10 mM CaCl$_2$ and 20% (w/v) polyethylene glycol 4000 was added, followed by a 20 min. incubation.

Protoplasts were precipitated by centrifugation and then resuspended to a concentration of about $5 \times 10^{10}$ protoplasts per ml in a solution (pH 6.8) containing 7 mM CaCl$_2$, 1.2 M sorbitol, 0.5 mg/ml yeast extract, 1 mg/ml peptone and 2 mg/ml glucose.

After incubation for 60 min. at 30° C., the protoplasts were centrifuged, washed with 0.6 M KCl solution and resuspended in 0.6 M KCl solution.

To select G418 resistant transformants, $1 \times 10^9$ protoplasts were plated in a 3% agar overlay on 2% minimal agar plates containing 2% glucose, 1.2 M sorbitol and 0.2 mg/ml G418. In order to simultaneously select for Lac+ transformants, $5 \times 10^8$ protoplasts were plated in 3% agar overlay on 2% minimal agar plates, Difco yeast nitrogen base medium, containing 2% lactose as the sole carbon source and 0.6 M KCl instead of 1.2 M sorbitol.

Colonies appeared within 4 to 5 days. On sorbitol plates without G418, protoplast regeneration was usually 0.2-0.5%, whereas on the 0.6 M KCl plates with glucose as carbon source this increased to 0.5-1.5%.

When G418 was used for selection, one transformant was obtained per $10^7$ regenerated protoplasts. Simultaneous selection on lactose plates yielded 10 transformants per $10^7$ regenerated protoplasts or 20 transformants per microgram of plasmid DNA (see Table, p. 21).

The presence of PTY75-LAC4 in the yeast cells could be proved by means of Southern hybridization with 32P-labeled pCR1.

DNA preparations were made according to Struhl et al. (Proc. Natl Acad. Sci. USA (1979) 76:1035-1039).

Example 5

Kluyveromyces lactis SD11 lac4 trp1 transformed to Trp+ with plasmid pKARS12

Cells of the strain K. lactis SD11 lac4 trp1 were transformed as described in Example 4 with 10 μg of pKARS12 DNA. Transformants were selected on 2% agar minimal plates containing 2% glucose and 0.6 M KCl. Per microgram of pKARS12 DNA, $3.4 \times 10^4$ Trp+ transformants were obtained.

Example 6

Kluyveromyces lactis SD69 lac4 transformed to Lac+ with plasmid pL4

K. lactis strain SD69 lac4 was transformed with plasmid pL4 using the same method as described for PTY75-LAC4 in Example 4. The transformants were selected on yeast nitrogen base plates (Difco) containing 2% lactose. The transformation frequency was 20 transformants per microgram of plasmid DNA.

Examples 7-13

Kluyveromyces lactis strains transformed to Trp+ with KARS-type plasmids

Analogous to the method described in Example 5, transformation experiments were carried out with other KARS-type plasmids. The results of the experiments are summarized in the following Table.

TABLE 1

| Ex. | Strain | Genotype | Plasmid | DNA | Transformants per microgram KARS fragments (kb) |
|---|---|---|---|---|---|
| 4. | SD69 | lac4 | PTY75-LAC4 | 20 | — |
| 7. | SD11 | lac4 trp1 | pKARS1 | $1.5 \times 10^3$ | 2.24 |
| 8. | SD11 | lac4 trp1 | pKARS2 | $5 \times 10^3$ | 1.24 |
| 9. | SD11 | lac4 trp1 | pKARS7 | $10^3$ | 2.3 |
| 10. | SD11 | lac4 trp1 | pKARS8 | $5 \times 10^3$ | 1.85 |
| 11. | SD11 | lac4 trp1 | pKARS10 | $2.4 \times 10^4$ | 3.15 |
| 12. | SD11 | lac4 trp1 | pKARS12 | $3.4 \times 10^4$ | 5.0 |

TABLE 1-continued

| Ex. | Strain | Genotype | Plasmid | DNA | Transformants per Size of microgram KARS fragments (kb) |
|---|---|---|---|---|---|
| 13. | SD11 | lac4 trp1 | pKARS13 | $1.5 \times 10^4$ | 2.0 |

The molecular weights of pKARS plasmids were determined after digestion with endonucleases EcoRI and HindIII, using an 0.8% agarose gel and standard molecular weight markers.

Example 14

Kluyveromyces lactis SD11 lac4 trp1 transformed to Trp+ with plasmids containing the KARS-2 sequence using a transformation procedure with whole cells Plasmid pEK2-7 (see FIG. 2) was used to transform K. lactis SD11. This plasmid consists of plasmid YRp7 into which a 1.2 kb fragment containing the autonomously replicating sequence derived from KARS-2 has been cloned. K. lactis SD11 was grown overnight at 30° C. in 1% yeast extract, 2% peptone and 2% glucose (pH 5.3). The cells were harvested at $OD_{610}$ nm of 4–8 by centrifugation at 1000xg for 5 min. The cells were washed with TE-buffer (10 mM Tris-HCl, 1 mM EDTA, pH 8.0) and the pellet was resuspended in TE-buffer at a concentration of $2 \times 10^8$ cells per ml. This suspension was diluted with one volume of 0.2 M LiCl and shaken at 30° C. for 60 min.

Plasmid pEK2-7 DNA (10 μg) was added to 0.1 ml of Li-treated cells and the incubation was continued at 30° C. for 30 min. One volume of 70% polyethylene glycol 7000 was added and the mixture was incubated for another 60 min. at 30° C. The mixture was exposed to heat treatment at 42° C. for 5 min. and the cells were plated onto minimal agar containing 2% glucose and 0.67% yeast nitrogen base (YNB). Transformants were observed after incubation at 30° C. for 36–48 hrs.

Example 15

Kluyveromyces fragilis transformed with plasmids containing the KARS-2 sequence

Two types of plasmids were used to transform K. fragilis. The first plasmid, pGB 180, was constructed by cloning the 3.5 kb BglII fragment from plasmid pEK2-7 (FIG. 2) containing the KARS-2 autonomously replicating sequence from K. lactis and the TRP1 gene from S. cerevisiae into the BamHI site of pJDB 207 (J.D. Beggs, Alfred Benzon Symposium (1981) 16:383). About 36 K. fragilis leu mutants obtained after UV-treatment of K. fragilis were transformed with pGB 180 by the Li+ method as described in Example 14. One mutant, K. fragilis leu 24, was transformed to Leu+ with a frequency of about $10^3$ transformants per μg of plasmid DNA.

The second plasmid, pGL2, was constructed by cloning the 3.5 kb BglII fragment from pEK2-7 as described above into the BamHI site of plasmid pACYC177 (Chang et al., J. Bacteriol. (1972) 134:1141–1156) which contains the transposon Tn601 conferring resistance to kanamycin and the gentamycin derivative G418. K. fragilis strain 21 was transformed with plasmid pGL2 by the Li+ method as described in Example 14. The transformed cells were plated onto YNPD-agar (YNB medium to which 2% dextrose and 2% agar was added) containing 50 μg of G418 per ml. Transformants were detected after incubation at 30° C. for 48 hours, whereas spontaneously resistant mutants were detected only after 6 days. DNA was extracted from K. fragilis transformants and transformed into suitable E. coli DG 75 cells. DNA extracted from kanamycin-resistant E. coli cells showed the presence of plasmid pGL2. These experiments show that K. fragilis strains can be transformed by plasmids containing KARS-sequences and that these plasmids are autonomously replicating in K. fragilis.

Example 16

Kluyveromyces lactis SD11 lac4 trp1 expressing preprochymosin and its various maturation forms after being transformed with plasmids containing the KARS-2 sequence, the structural genes encoding preprochymosin and its various maturation forms, and various promoters directing the expression of the structural genes This Example comprises a number of steps the most essential of which are:
1. Addition of SalI linkers in front of the cloned structural genes encoding preprochymosin, prochymosin, pseudochymosin and chymosin.
2. Introduction of a DNA fragment in plasmids obtained above containing the KARS-2 autonomously replicating sequence from K. lactis and the TRP1 gene from S. cerevisiae.
3. Introduction of various promoters, which direct the synthesis of the various maturation forms of preprochymosin, into the plasmids obtained above.

Starting materials for the expression of bovine preprochymosin and its various maturation forms in K. lactis were the following cloned structural genes:
pUR1531: methionyl-pseudochymosin
pUR1522: methionyl-prochymosin
pUR1523: methionyl-preprochymosin
pUR1524: methionyl-preprochymosin The construction and structure of these plasmids has been described in detail in European Patent Application No. 82 201272.0, published on Apr. 20, 1983, EPA Serial No. 0 077 109, which disclosure is herein incorporated by reference. The genes were isolated and the plasmids constructed as described in the above reference.

A. Introduction of SalI linkers in plasmids pUR1531, pUR1522, and pUR1523 and pUR1524 (FIG. 1)

The plasmids pUR1531, pUR1522, pUR1523, pUR1524 contain an EcoRI restriction site just in front of the ATG initiation codon. Because an additional EcoRI site was present within the chymosin gene, a SalI linker molecule was introduced just in front of the first EcoRI site to facilitate the introduction of various promoter sequences directing the expression of the distal structural genes.

About 50 μg of DNA was incubated with 50 units of endonuclease EcoRI in the presence of 125 μg/ml ethidium bromide in 10 mM Tris-HCl, 50 mM NaCl, 6 mM betamercaptoethanol, 10 mM $MgCl_2$ and 100 μg/ml bovine serum albumin, pH 7.5, at 37° C. for 60 min. Plasmid DNA was predominantly converted to linear and circularized linear molecules under these conditions. The DNA was extracted with one volume of phenol and one volume of chloroform and precipitated with one volume of 2-propanol.

The DNA was dissolved in TE-buffer and completely digested with endonuclease SalI. A DNA fragment of about 1800 bp was isolated from an agarose gel by electroelution. The fragments were extracted with phenol and chloroform and precipitated with 2-propanol. The precipitates were dissolved in TE-buffer. The cohesive ends were filled-in with DNA polymerase as follows: To 15 μl containing the 1800 bp DNA fragment (about 1–2 μg) was added 1 μl of a 2 mM solution of dATP, dGTP, dCTP and dTTP, 6.5 μl of 4x nick-buffer containing 0.2 M Tris-HCl (pH 7.2), 40 mM MgSO$_4$, 4 mM dithiothreitol, 200 mg/ml bovine serum albumin, and 2.5 μl of water. Two units of DNA polymerase (Klenow fragment) were added and the mixture was incubated at 20° C. for 30 min. DNA polymerase was then inactivated by heating at 70° C. for 5 min. A phosphorylated SalI-linker (prepared as described in Maniatis et al., *Molecular Cloning*, (1982) Cold Spring Harbor Laboratory was added to this mixture together with T4 DNA ligase (10$^3$ Units) and ATP. After incubation at 22° C. for 4 hours the mixture was incubated at 4° C. for an additional 16 hours. The mixture was then incubated with endonucleases SalI and HindIII and a DNA fragment of about 1500 bp was recovered from an agarose gel by electroelution. The fragments (A, B, C, D) were purified by phenol and chloroform extraction followed by precipitation with 2-propanol. These fragments were ligated to a 3.3 kb HindIII-SalI fragment (about 0.5 μg) derived from plasmid pPA153-209 (Andreoli, *Mol. Gen. Genetics* (1985) 199:372) containing a temperaturesensitive replicon and an ampicillin resistant gene (encoding beta-lactamase), and purified from an agarose gel by electroelution. The ligated molecules were transformed into *E. coli* HB 101. Ampicillin-resistant, tetracycline-sensitive clones were cultured and the plasmid DNA extracted. Digestion of plasmid DNA with endonucleases SalI, EcoRI and HindIII confirmed that the plasmids pGB131, pGB122, pGB123 and pGB124 (FIG. 1) were obtained.

B. Introduction of a KARS-2 and TRP1 gene in the plasmids pGB131, pGB122, pGB123, pGB124, respectively Autonomously replicating sequences derived from and replicating in Kluyveromyces were obtained as described in Examples 2 and 7–15. The autonomously replicating sequence in plasmid pKARS-2 is located on a 1.24 kb fragment and this fragment was cloned into the well-known plasmid YRp7 and a new plasmid pEK2-7 was obtained (FIG. 2). Digestion of pEK2-7 with endonuclease ClaI resulted in fragments of 3.5 and 5.5 kb, respectively. The 3.5 kb fragment containing both the TRP1 gene derived from *S. cerevisiae* and the KARS-2 sequence derived from *K. lactis* (FIG. 2) was isolated from an agarose gel by electroelution and ligated to ClaI-digested plasmids pGB131, pGB122, pGB123 and pGB124. The resulting mixture was transformed into *E. coli* JA300 (trpC). Characterization of plasmid DNA extracted from Trp$^+$ transformants confirmed the construction of plasmids pGB151, pGB152, pGB153 and pGB154 (FIG. 2).

C. Introduction of various promoter sequences in the plasmids directing the synthesis of the various maturation forms of preprochymosin The SalI-digested plasmids containing the KARS-2 sequence, the TRP1 gene and the structural gene of preprochymosin or its various maturation forms are well suited to accept SalI-linked promoter sequences to direct the synthesis of the distal structural gene in *K. lactis* transformants. In most cases the promoter sequences have to be provided with SalI linkers. Any promoter sequence can be provided with such a SalI linker and in the following Examples this is illustrated with:
1. the isocytochrome cI promoter from *S. cerevisiae*
2. the lactase promoter from *K. lactis*.

C1. Addition of SalI linkers to the isocytochrome cI promoter from *S. cerevisiae* and introduction into plasmids Plasmid pYeCYC1 consisting of the isocytochrome cI gene cloned into plasmid pBR322 was used as the starting material (G. Faye et al., *Proc. Natl. Acad. Sci. USA* (1981) 78:2258). From nucleotide sequence data it is known that an EcoRI site is present in the isocytochrome cI gene at nucleotide +8 (Ibid.). Plasmid pYeCYCI was cleaved with endonuclease EcoRI, ligated with T4 DNA ligase and transformed into *E. coli* HB101, yielding a plasmid pC15 containing the 1930 bp fragment carrying the promoter and 8 nucleotides of the isocytochrome cI gene.

Plasmid pC15 was cleaved with endonuclease EcoRI and incubated briefly with nuclease Bal31 to remove just a few nucleotides. The Bal31 digested ends were converted to blunt-ends with DNA polymerase (Klenow fragment) and a phosphorylated EcoRI linker was ligated to this DNA. After incubation with endonuclease EcoRI, ligation and transformation into *E. coli*, a transformant, pC15-R12, was identified in which 12 nucleotides from the cytochrome cI gene had been removed. A SalI linker was introduced by cleaving plasmid pC15-R12 with endonuclease EcoRI, filling in the cohesive ends with DNA polymerase, ligation of a phosphorylated SalI linker, incubation with endonuclease SalI and recloning the resulting 1070 bp fragment in the SalI digested plasmids pGB151, pGB152, pGB153 and pGB154, respectively. This yielded the isocytochrome cI promoter-containing plasmids pGB161, pGB162, pGB163 and pGB164 (FIG. 3), respectively, as identified by colony hybridization with the $^{32}$P-labeled 1070 bp fragment as probe. Plasmid DNA was prepared from the positive clones and the correct orientation of the isocytochrome cI promoter was confirmed by the presence of a 850 bp fragment after digestion with endonuclease SmaI.

C2. Addition of SalI linkers to the lactase promoter from Kluyveromyces lactis and introduction into plasmids The starting material was plasmid pK16 containing the lactase gene from *K. lactis* cloned into the EcoRI site of plasmid pBR322 (R. C. Dickson and J. S. Markin, *Cell* (1978) 15:123). Sequencing of large parts of the lactase structural gene and its promoter established the presence of a ClaI site at about 450 bp in the lactase structural gene. Plasmid pK16 was digested with endonuclease ClaI and the fragment containing the promoter and about 450 bp of the structural gene were recloned into the plasmid pBR322 digested with endonucleases ClaI and AccI (partially). In one plasmid, pGB182, the retained ClaI site at about 450 bp in the lactase structural gene was opened by incubation with endonuclease ClaI and trimmed by incubation with nuclease Bal31. The Bal31 ends were rendered blunt-ends by incubation with DNA polymerase. A phosphorylated EcoRI linker was ligated to this trimmed fragment. Digestion with endonuclease EcoRI and recloning of the trimmed fragment resulted in the plasmid pGB183, which had retained the lactase promoter but was devoid of the structural gene. SalI linkers were added to this fragment as described above (see Example 16.C1). The SalI-linked lactase promoter was ligated to SalI-cleaved plasmids pGB151, pGB152, pGB153 and pGB154, respectively, yielding plasmids pGB171, pGB172, pGB173 and pGB174, respectively.

Plasmids obtained as described in this Example 16 were introduced into *Kluyveromyces lactis* SD11 lac4 trp1 by the Li+ method as described in Example 14, and Trp+ transformants selected for. The presence of preprochymosin or its maturation forms in Kluyveromyces extracts was demonstrated by immunological ELISA techniques e.g., by spotting aliquots of the extracts on nitrocellulose filters and assaying the filters as described by D. J. Kemp and A. F. Cowman (*Proc. Natl. Acad. Sci. USA* (1981) 78:4520–4524).

Cell-extracts were prepared as follows: *K. lactis* transformants were grown at 30° C. for about 16–24 hours in YNB-medium containing 2% dextrose. Cells were harvested at $OD_{610nm}$ between 2.2–6.0 by centrifugation at 6000 rpm for 10 min. in a Sorvall G-S3 rotor. The pellet was resuspended in sterile distilled water to $OD_{610}$ nm of 600 and chilled on ice. 0.5 ml of this cell suspension was diluted with 0.5 ml of ice-cold water and mixed with 2 g of Ballotini Beads (diameter 0.25–0.35 mm; Braun-Melsungen GMBH, GFR). The cells were disrupted by shaking for 4 min on a Vortex shaker at maximum speed. More than 95% of the cells were disrupted by this method as verified by phase contrast microscopy. Cell debris was removed by centrifugation for 1 min in an Eppendorf centrifuge. Aliquots of the extracts were frozen in liquid nitrogen and stored at −80° C.

1–5 µl aliquots of the cell extracts were spotted on nitrocellulose membrane filters. The filters were dried, wetted with 192 mM glycine, 25 mM Tris, 20% ethanol (pH 8.3) and incubated for 60 min. at 22° C. The filters were subsequently incubated with preincubation buffer (0.35M NaCl, 10 mM Tris-HCl (pH 7.6), 2% bovine serum albumin) for 30 min. The filters were washed 3 times for 5 min with RIA-buffer (0.125M NaCl, 10 mM Tris-HCl, pH 7.6, 0.1 mM PMSF, 1% Triton X-100, 0.5% sodium desoxycholate, 0.1% sodium dodecylsulfate (SDS) and 0.3% gelatin). The filters were incubated overnight at 4° C. in 1 ml RIA buffer containing 10 µl of chymosin antiserum. Antiserum was removed by washing with RIA buffer (three times) and incubated with 1 µCi $^{125}$I-protein A in 1 ml of RIA-buffer for 60 min at 22° C. $^{125}$I-protein A was removed by washing with RIA buffer (5 times). The filters were dried and autoradiographed overnight. The presence of preprochymosin or its maturation forms in *K. lactis* transformants was clearly observed.

The presence of chymosin activity in cell extracts from *K. lactis* transformants was determined by high performance liquid chromatography (HPLC) as described by A. C. M. Hooydonk and C. Olieman, *Netherl. Milk Dairy* (1982) 36:153. 50 µl of enzyme solution or extract was added to 1 ml of a 10% solution of milkpowder (Difco) in 10 mM $CaCl_2$. The solution was incubated for 15 min. at 31° C. The reaction was stopped by adding 2 ml of 12% trichloroacetic acid (TCA). Almost all proteins are precipitated by TCA except glycomacropeptide (GMP) that has been cleaved from K casein by chymosin action. Denatured proteins were pelleted by centrifugation and 1 ml of the clear supernatant was neutralized with 0.4 ml of 1N NaOH. The solution was centrifuged again and the amount of GMP produced was detected with HPLC, monitoring the extinction coefficient at 214 nm. Extracts from *K. lactis* transformants containing prochymosin were first incubated at pH 2 for 2 hours and subsequently neutralized before performing the chymosin activity test. Chymosin was found only after the pH 2 treatment.

Example 17

Construction of chymosin expression plasmids containing a long lactase promoter sequence A. Construction of pUCla56

Chromosomal DNA was isolated from *Kluyveromyces lactis* strain CBS 2360 (Das and Hollenberg, *Current Genetics* (1982) 5:123–128), cleaved with XhoI, and separated according to size on a sucrose gradient. Fractions containing the lactase gene were detected with a LAC4 probe from plasmid pK16 (see Example 16.C2) after spotting the DNA on a nitrocellulose filter. DNA containing the LAC4 gene was cloned into the XhoI site of plasmid pPA153-215 (Andreoli, *Mol. Gen. Gen* (1985) 199:372-380) giving rise to plasmid pPA31. An XbaI fragment of pPA31 containing the lactase gene was subcloned in the XbaI site of pUC19 (Yanisch-Perron et al., *Gene* (1985) 33:103–119) which yields plasmid pUCla56.

Figure 4:
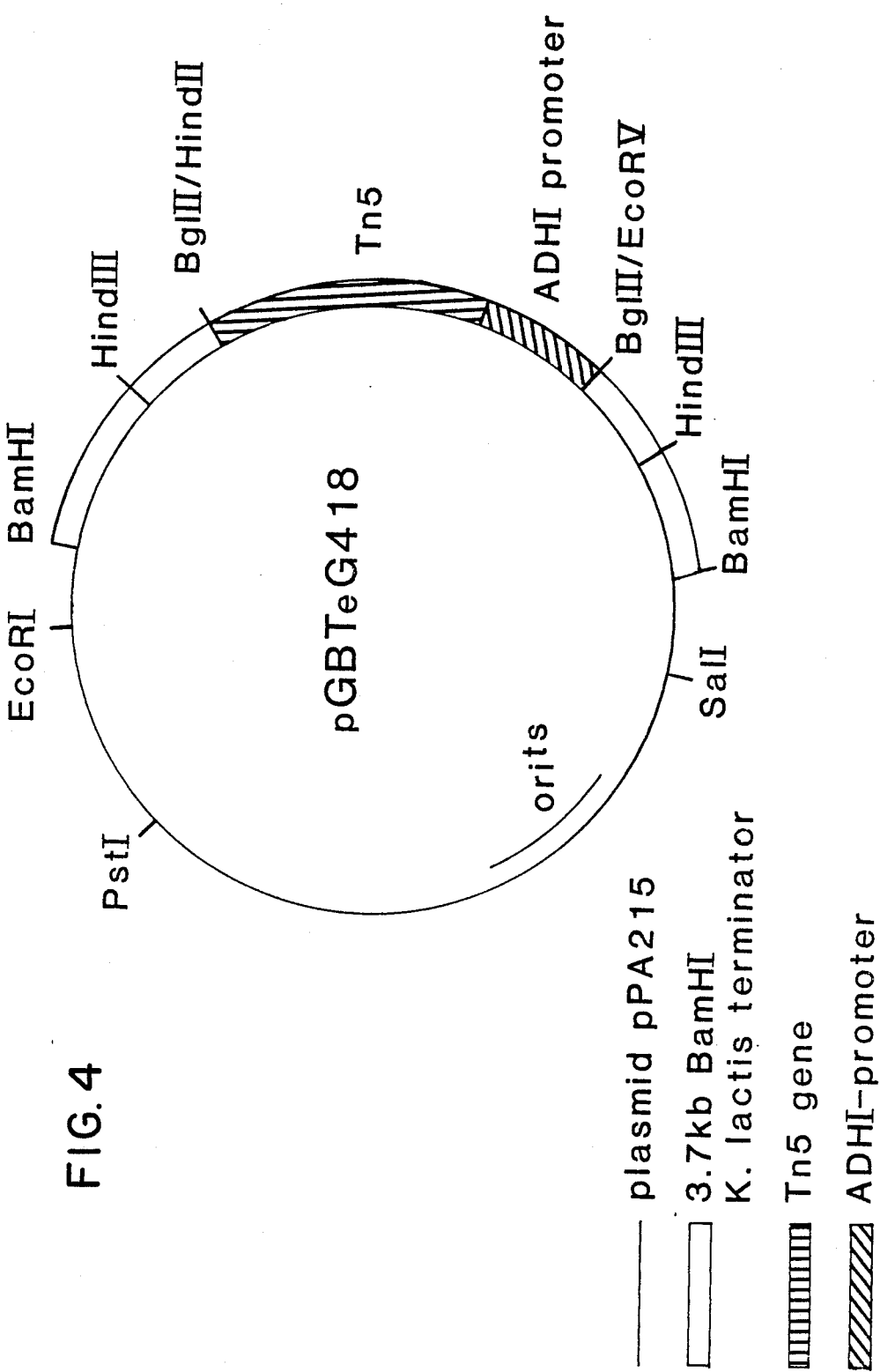
FIG. 4 is a description of the plasmid pGBTe418.

B. Introduction of the G418 resistance gene in the terminator of the lactase gene The terminator fragment containing the G418 resistance marker was obtained from plasmid pGBTeG418. *E. coli* containing pGBTeG418 were deposited at Centraal Bureau voor Schimmelcultures under number CBS184.87 on Feb. 26, 1987. Plasmid pGBTeG418 (see FIG. 4) consists of the plasmid pPA153-215 as described (Andreoli, *Mol. Gen. Gen.* (1985) 199:372-380), and a 5.6 kb fragment consisting of the 3.7 kb BamHI *K. lactis* lactase terminator fragment (Breunig et al., *Nucl. Acid Res.* (1984) 12:2327-2341) and the Tn5 gene (Reiss et al., *EMBO J.* (1984) 3:3317) conferring resistance to gentamycin G418 under the direction of the promoter alcohol dehydrogenase I (ADH) from yeast, similar to that described by Bennetzen and Hall, *J. Biol. Chem.* (1982) 257:3018-3025.

C. Construction of plasmids containing the G418 resistance gene and chymosin encoding DNAs The 3.6 kb HindIII-XbaI fragment from plasmid pGBTeG418 containing the G418 resistance gene (see Example 17B) and the SalI-HindIII fragment containing the prochymosin gene from pGB123 were ligated in pUC19 cleaved with SalI and XbaI. This yielded plasmid pGB900.

D. Construction of plasmid pGB901

Plasmid pGB901 was constructed by ligating the following four fragments:
(1) A 3.6 kb XbaI-HaeII fragment containing the lactase promoter to about position −90 from the lactase ATG start codon isolated from pUCla56,
(2) a HaeII-SalI fragment of about 70 bp which extends from the above HaeII site to a SalI site which was ligated to position −26 in a similar Bal31 experiment as described in Example 16.C2. However, only a SalI linker was used in the present case.

(3) the 5.1 kb SalI-XbaI fragment containing prochymosin and G418 from pGB900 (see Example 17C),
(4) pUC 19 cleaved with XbaI.

During the construction of the plasmid the CG sequence from the HaeII site was inadvertently removed, thereby creating a HindIII site at this position.

Prochymosin-encoding DNA is present in plasmid pGB901. This may readily be converted to plasmids with preprochymosin, pseudochymosin or chymosin DNA by using the SalI-BglII fragments from pGB 131, 122 or 124, respectively.

Example 18

Secretion of prochymosin from Kluveromyces lactis transformants

To direct the synthesis of prochymosin in Kluyveromyces, plasmid pGB901 was used to transform *K. lactis* strains SD11 and CBS2360 with similar results. The transformation was carried out essentially as described in Examples 4 and 14 by using intact plasmid DNA or plasmid DNA cut with restriction endonucleases. In the latter case restriction endonucleases were used which cut in the promoter region, e.g., SacII, NdeI, SnaBI or SpeI, or in the terminator region, e.g., EcoRV, or both the promoter and terminator regions.

*K. lactis* strains CBS2360 and SD11 were grown in 100 ml of YEPD medium containing 2.5 ml 10xYNB to $OD_{610}$ of 0.75. After collecting and washing the cells and incubating with 0.1 M lithium acetate, 15 μg of plasmid DNA, cut at the unique SacII site in the lactase promoter, was added to the cells. After a heat shock of 5 min at 42° C., the transformed cells were spread on agar plates containing 15 ml of YEPD agar with 50 μg/ml of G418 and were overlayered 1 hr before use with 15 ml YEPD without G418. Colonies were grown for 3 days at 30° C.

In one of the experiments *K. lactis* strain CBS2360 was transformed with pGB901, linearized by cutting with SacII. Transformants were selected on G418 containing agar plates and grown at 30° C. in YEPmedium containing 2% galactose. After 60 hours, cells and medium were separated by centrifugation. Cells were disrupted by treatment with glass beads. Culture medium and cell extract were treated at pH 2 before assaying for chymosin activity. Foltman, *Methods in Enzymology* (1970) 19:421–426.

Cells were removed from cultures by centrifugation and the resulting supernatants were acidified to pH 2 by the addition of 1 M $H_2SO_4$ and incubated for 2 hours at room temperature. The solutions were then neutralized to pH 6 by the addition of 2 M Tris base. A 50 μl volume of an appropriate dilution was added to a suspension of 12% non-fat dry milk in 10 mM $CaCl_2$ and incubated at 37° C. until a clot formed. A unit of chymosin activity is defined as the amount of active chymosin required to produce a clot in 10 min. under these conditions. The supernatant contained milk-clotting activity due to the production and secretion of prochymosin by *K. lactis* transformants although no signal sequence for protein secretion was added to prochymosin. About 30–60% of the total prochymosin produced was found in the medium as determined by the above-described milk-clotting assay. Similar results were obtained when *K. lactis* strain SD11 was used.

Example 19

Construction of lactase-chymosin fusion proteins giving enhanced chymosin expression By taking various SnaBI - SalI fragments (from a Bal31 experiment similar to the one described in Example 16.C2 but using a single SalI linker only) variants of pGB901 containing a fusion between the lactase and chymosin proteins were obtained (Table 2). The extra amino acids provided by lactase DNA and linker sequences can be removed, along with the pro sequence of prochymosin, by treatment with acid. It was observed that a fusion containing 4 amino acids from the lactase coding sequence (pGB902) resulted in enhanced chymosin production.

TABLE 2

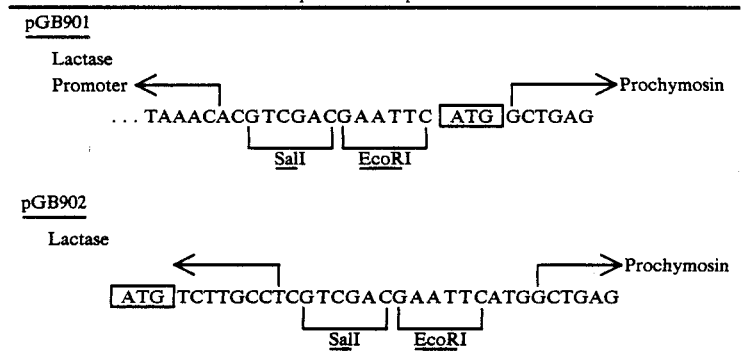

Protein synthesis starts at the boxed ATG codon.

Example 20

Secretion of preprochymosin by Kluyveromyces transformants

The SalI site from the polylinker of pGB902 (see Example 19) was removed for convenience. pGB902 was partially digested with SalI, followed by a short incubation with Bal31 (Boehringer). Linear fragments were isolated from an agarose gel, ligated and transformed into *E. coli*. A correct plasmid, pGB903, was obtained. Restriction analysis showed that this plasmid also has the XbaI and HindIII sites removed from the polylinker.

To construct a plasmid containing and expressing preprochymosin, plasmid pGB903 was digested with the restriction endonucleases SalI and BglII. The 11 kb DNA fragment was isolated from an agarose gel by electroelution. Similarly, plasmid pGB124 (see Example 16) containing the preprochymosin gene was digested and the 0.3 kb SalI-BglII fragment containing the N-terminal part of the preprochymosin gene was isolated. The 11 kb and the 0.3 kb DNA fragments were mixed, ligated with DNA ligase and transformed into E. coli. Plasmid pGB904 was isolated which contained the preprochymosin gene fused to a small part of the lactase gene (Table 3).

TABLE 3

Nucleotide Sequence at the Junction Between the Lactase Promoter and Preprochymosin in pGB904 pGB904

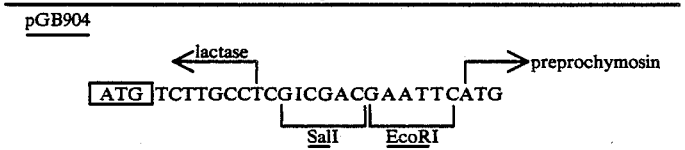

Protein synthesis starts at the boxed ATG codon.

K. lactis CBS2360 cells were transformed with pGB904, which had been linearized with SacII. Transformants were selected, grown and assayed for chymosin activity as described in Example 18. In the following Table a comparison is made between K. lactis CBS2360 cells transformed with pGB902 (see Example 19) and with pGB904. Chymosin production is expressed in arbitrary units per ml of cells at $OD_{610}$ of 200.

TABLE 4

Secretion of Prochymosin by K. Lactis Cells Transformed With pGB902 and pGB904

| Transformant | pGB902 | | pGB904 | |
| --- | --- | --- | --- | --- |
| | Supernatant | Pellet | Supernatant | Pellet |
| 1 | 3.2 | <0.4 | 22.4 | 1.7 |
| 2 | 1.3 | <0.4 | 33.3 | 3.0 |
| 3 | 7.1 | 1.4 | 28.0 | 2.3 |
| 4 | 4.4 | 0.66 | 53.8 | 5.8 |

Example 21

Secretion of prochymosin by Kluyveromyces using heterologous leader sequences

A. Chemical synthesis of an amyloglucosidase leader sequence and construction of a plasmid containing said leader sequence The leader sequence of amyloglucosidase (AG) from *Aspergillus awamori* was published by Innis et al., Science (1985) 228:21-26. Based on the protein sequence, oligonucleotides were derived to permit insertion of the leader sequence in front of the prochymosin gene (see FIG. 5).

The oligonucleotides were synthesized with an Applied Biosystems DNA synthesizer. The oligonucleotides were purified by electrophoresis on a denaturing polyacrylamide gel, then electroeluted from the gel.

Plasmid pGB903 (see Example 20) was cut at the unique SalI site. The oligonucleotides were hybridized at 65° C., 50° C. and 37° C. for one hour each in 2×SSC. The oligonucleotides had no phosphate at the 5' end to prevent formation of multimers. The DNA was ligated into the SalI site using T4 polynucleotide ligase. The ligation mixture was transformed into E. coli HB101. Twenty-four of the colonies were cultured and plasmid DNA isolated. One of the plasmids, pGB905, was shown to have the correct orientation of the oligonucleotides by restriction enzyme analysis. Plasmid pGB905 was transformed to K. lactis CBS2360. Chymosin production was analyzed according to the procedure described in Example 18. The results are shown in the Table below.

Chymosin production, in arbitrary units/ml of cells of $OD_{610}$ at 200, is shown in the following Table.

TABLE 5

Secretion of Prochymosin by K. Lactis Cells Transformed with pGB902 and pGB905

| Transformant | 902 | | 905 | |
| --- | --- | --- | --- | --- |
| | Sup. | Pellet | Sup. | Pellet |
| 1. | 3.2 | <0.4 | 60.6 | <0.4 |
| 2. | 1.3 | <0.4 | 56.4 | <0.4 |
| 3. | 7.1 | 1.4 | 56.7 | <0.4 |
| 4. | 4.4 | 0.66 | 57.6 | <0.4 |

B. Chemical Synthesis of a Novel Synthetic Leader Sequence into Contruction of a Plasmid Containing the Novel Synthetic Leader Sequence A synthetic leader sequence was prepared which has a sequence different from any known known leader sequence. Using this leader sequence, all prochymosin synthesized was secreted by Kluyveromyces as shown below.

The synthetic leader sequence was devised using frequently occuring amino acids from position −6 to +2 of the signal sequence cleavage site (Von Heyne, *Eur. J. Biochem.* (1983) 133:17-21). Frequently occuring yeast codons were also employed and extra nucleotides were incorporated in front of the ATG sequence to make up for the deletion of 26 nucleotides in pGB902. The oligonucleotides used and the resulting leader sequence are shown in FIG. 6.

The synthetic leader sequence DNA was synthesized within an Applied Biosystems DNA synthesizer. The resulting oligonucloetides were run on a 40 cm long, 1 mm thick polyacrylamide gel, containing TBE buffer (50 mM Tris, 50 mM borate, 1 mM EDTA, pH 8.3) and 7 M urea until the bromphenol had traveled 2/3 of the gel length. The DNA was visualized, eluted from the gel and precipitated with ethanol.

Also from pGB901 a derivative was made with a deletion around the SalI site resulting from the polylinker of pUC19. This was done by replacing the 0.5 kb SnaBI-BglII fragment from pGB903 by the corresponding fragment from pGB901. The resulting plasmid was cut at the unique SalI site. The oligonucleotides were hybridized at 65° C., 50° C. and 37° C. for one hour each in 2×SSC. The DNA was ligated into the SalI site using T4 polynucleotide ligase. The plasmid was then transformed into E. coli HB101. Of the colonies obtained, 24 were cultured and plasmid DNA isolated. One of the plasmids, pGB906, was shown to have the nucleotides in the correct orientation by restriction enzyme digestion. It was found that *K. lactis* transformed with pGB906 secreted more than 95% of the prochymosin produced.

C. Analysis of Chymosin Protein Produced by *K. lactis* Transformed with pGB905

Figure 7:
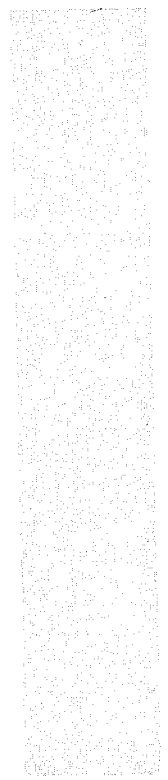
FIG. 7 is an immunoblot showing the production of prochymosin in *K. lactis*.

Transformants were grown for 3 days at 30° C. and samples were collected from the supernatant of the cultures. Protein samples were electrophoresed on a polyacrylamide gel according to Laemmli (*Nature* (1970) 227:680–685). Proteins were blotted onto a nitrocellulose filter according to the method of Towbin et al. (*Proc. Natl. Acad. Sci. USA* (1979) 76:4350–4354). Chymosin protein was detected by incubating the filter with a polyclonal antiserum against chymosin (Chr. Hansen), followed by donkey anti-rabbit antibodies coupled to a peroxidase (Amersham) and finally with 0.6 mg/ml 4-chloronaphthol and 0.015% hydrogen peroxide in a buffer solution (50 mM Tris-HCl pH 7.5, 0.9% NaCl) containing 40% methanol Prochymosin excreted by the AG signal sequence is correctly cleaved after pH 2 treatment as demonstrated by this assay (FIG. 7).

Example 22

Construction of plasmids containing the *Saccharomyces cerevisiae* α-factor sequence for efficient secretion

A. Saccharomyces α-factor Expression Plasmids

1. Construction of Plasmids pDM100-PC: The starting material was plasmid pGB163 (see Example 16.C1, above). Plasmid pGB163 was digested with BamHI and ligated to an XbaI-BamHI, α-factor leader-prochymosin adaptor. The resulting mixture was then treated with PstI and a 96 bp fragment encoding the pro-α-factor processing site and the N-terminal region of prochymosin was isolated. A 1900 bp fragment encoding bovine prochymosin was isolated from plasmid pJS111 following digestion with PstI and SalI. Plasmid pJS111 is a pBR322 derivative containing the prochymosin gene from pGB163 under the regulatory control of the ADH-2 promoter and the glyceraldehyde 3-phosphate (GAP) terminator. The 1900 bp PstI to SalI fragment that was removed contains the prochymosin gene and the GAP terminator. The yeast GAP 49 gene promoter and transcription terminator are essentially as described by Travis, *J. Biol. Chem.* (1985) 260:4384–4389.

Plasmid pDM100, containing a fusion of the GAP promoter the *S. cerevisaie* α-factor leader, and a synthetic gene for human γ-interferon flanked by XbaI and SalI sites and the α-factor terminator, was digested with XbaI and SalI, treated with alkaline phosphatase, then ligated to the 96 bp and 1900 bp fragments described above. The α-factor leader and terminator are essentially as described by Brake, *Proc. Natl. Acad. Sci. USA* (1984) 81:4642–4646. The resulting plasmid pDM100-PC was isolated and contained a fusion of the GAP promoter, the α-factor leader and prochymosin gene. The complete sequence of the BamHI insert is shown in FIG. 8.

To allow selection of yeast transformants, two plasmids, pKS100 and pAB300, were constructed.

pKS100: pKS100 was constructed by insertion into pDM100-PC of an 1170 bp HindIII fragment from YEp24 containing the *S. cerevisiae* URA3 gene.

pAB300: pAB300 was produced by insertion into pDM100-PC of a 3500 HindIII-SalI fragment from pGB901 containing the 3' region of the *K. lactis* LAC4 gene and the G418 resistance marker. The GAP/α-factor/Prochymosin BamI insert in pDM100PC is illustrated in FIG. 8.

2. Transformation of *K. lactis* and *S. cerevisiae*

Plasmid pKS100 was digested at the BglII site in the prochymosin coding region and used to transform *K. Lactis* strain KRN201-6. This strain is a derivative of strain 2UV21 (a lac4 trp1 ura3 [kil⁰]) in which the lac4 gene has been replaced by the LAC4 promoter-prochymosin gene fusion from pGB901. Integration of pKS100 is thus targeted to the integrated prochymosin coding region. Plasmid pKS100 was also used to transform *S. cerevisiae* strain AB110 (α ura3 leu2 his4 pep4-3 [cir⁰]), in this case targeting to the SacII site in the 3' region of the GAPDH gene.

The resulting transformants were grown to saturation in liquid YEPD medium, and the culture supernatants and cell lysates assayed for chymosin activity after activation at pH 2. As shown by the results summarized in Table 6 below, the *K. lactis* transformants efficiently secreted prochymosin into the medium, whereas the *S. cerevisiae* transformants secreted only a small fraction of the prochymosin produced.

TABLE 6

Prochymosin Production in *K. lactis* and *S. cerevisiae* Transformants

| Strain | Chymosin Activity (relative units/ml culture) | |
|---|---|---|
|  | Cell Extract | Culture Supernatant |
| AB110 | <0.25 | <1.0 |
| AB110::pKS100 | 15.5 | 2.3 |
| KRN201-6 | <0.25 | <1.0 |
| KRN201-6::pKS100 | 12.0 | 333.0 |

Plasmid pAB300 was used to transform *K. lactis* strain 2UV21 to G418 resistance, targeting integration to the EcoRV site in the 3' region of the LAC4 gene. These transformants were also found to efficiently secrete prochymosin into the culture medium as shown in Table 7 below.

TABLE 7

Prochymosin Secretion From α-Factor/Prochymosin Fusions

| Host Strain | Transforming Plasmid | Secreted Chymosin Activity (relative units/ml culture) |
|---|---|---|
| 2UV21 | — | <2 |
| KRN201-6 | — | <2 |
| KRN201-6 | pKS100 | 385 |
| 2UV21 | pAB300 | 294 |

B. Construction of LAC4 Promoter-α-Factor Leader-Prochymosin Fusions

In order to produce this fusion, two intermediate plasmids were constructed. Plasmid pDM100-PC was partially digested with PstI, ligated to a SalI-PstI adaptor encoding a portion of the α-factor leader and 26 bp of the region 5' to the LAC4 gene, and then digested with HindIII. A 1500 bp fragment was isolated from this mixture and then cloned into pUC18 digested with HindIII and SalI to produce pKS102.

A synthetic *E. coli* lac operator was ligated into the SalI site just 5' to the α-factor leader coding sequence in pKS102 to produce the plasmid pKS103. This was done because the LAC4 promoter-α-factor leader-prochymosin fusion may be toxic to *E. coli*.

Figure 9:
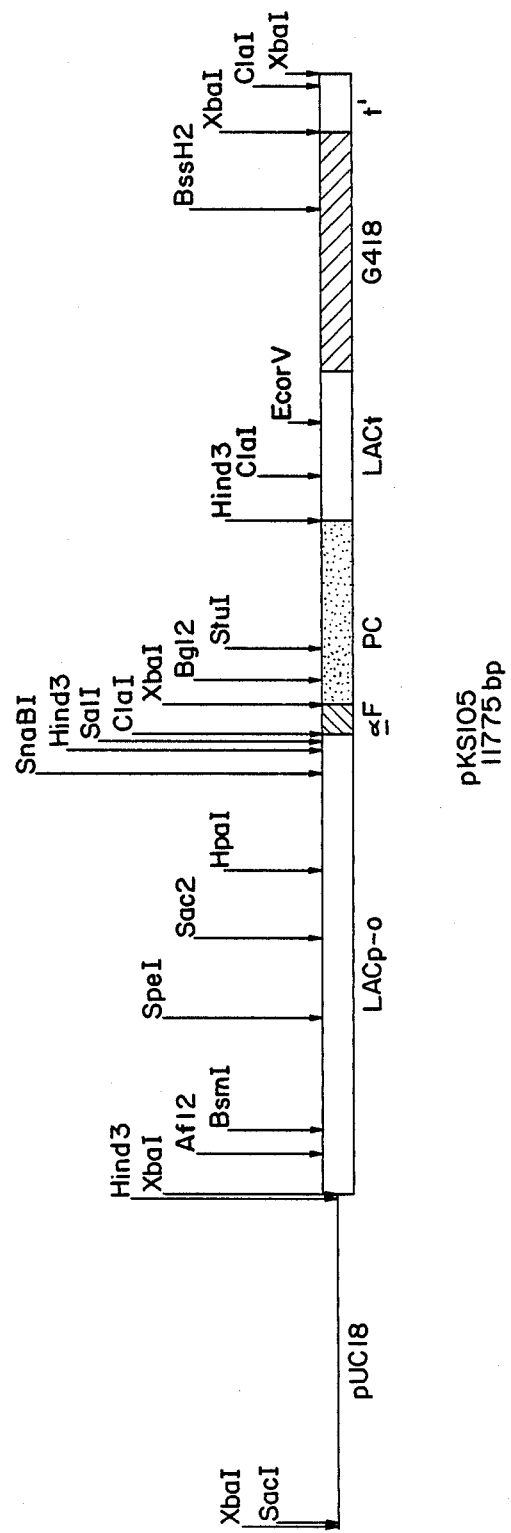
FIG. 9 is a restriction map of plasmid pKS105.

A 490 bp SalI-BglII fragment from pKS103 was isolated and ligated to SalI-BglII-digested pJD15R. pJD15R is derived from pGB901 by deletion of the SalI site in the pUC19 polylinker by filling-in to produce pJD15, and then recloning the 8800 bp XbaI fragment in the opposite orientation. From this reaction the plasmid pKS105 was isolated. These plasmids are illustrated in FIG. 9.

Plasmid pKS105 was then used to transform K. lactis strain CBS2360 to G418 resistance, using the SacII site in the LAC4 5' region as a targeting site for the integrative transformation. Chymosin production is expressed in units per ml of cells at $OD_{610}$ of 200 (Table 8).

TABLE 8

Secretion of Prochymosin by K. Lactis Cells Transformed with pKS105*

| Transformant | Supernatant | Pellet |
| --- | --- | --- |
| 1 | 111 | 3.3 |
| 2 | 147 | 4.5 |
| 3 | 124 | 3.7 |
| 4 | 125 | 3.0 |

*Chymosin activity in relative units/ml culture.

Example 23

Isolation and use of K. lactis α-factor signal sequence

Biological assays of culture supernatants were carried out as described (Julius, et al, Cell (1983) 32:839) using as a tester strain the S. cerevisiae Mata sst2-3 strain RC687. K. lactis strain CBS141 (α) was grown in medium consisting of 0.5% glucose, 0.17% yeast nitrogen base without ammonium sulfate (Difco), and 0.002% ammonium sulfate. After removal of cells by centrifugation, acetic acid was added to the culture supernatant to a concentration of 0.1 M, and the supernatant was passed over a column of BioRex 70 (Biorad). The column was washed with 0.1 M acetic acid and then the α-factor was eluted with 80% ethanol/10 mM HCl. The eluate was evaporated to dryness and then dissolved in 0.1% trifluoroacetic acid (TFA)/20% acetonitrile and applied to a reverse=phase HPLC guard column. The column was washed stepwise with solutions containing 0.1% TFA and 20%, 40%, 60% and 80% acetonitrile. The 60% fraction, containing the α-factor activity, was then applied to an analytical C-18 HPLC column and eluted with a gradient of 20% to 80% acetonitrile in 0.1% TFA. Fractions were collected and assayed for α-factor activity. The fractions containing α-factor activity were dried and subjected to amino acid sequence analysis.

Hybridization screening of plasmid libraries

Pools of oligonucleotides were labeled using α-[$^{32}$P]-ATP and T4 polynucleotide kinase. These oligonucleotide probes were used to probe Southern blots or bacterial colonies at 42° C. in the following hybridization solution: 4×SSC, 50 mM $KH_2PO_4$ pH 7, 1% sarkosyl, 10% dextran sulfate, 200 μg/ml sonicated, denatured salmon sperm DNA. Filters were washed in 2×SSC, 0.1% SDS at 42° C.

A plasmid library in the vector pJS109, containing inserts resulting from a limited Sau3AI digest of genomic DNA from K. lactis strain SD11 (a trpl lac4), size-fractionated to purify fragments >5000 bp was screened with these probes by plating transformants of E. coli strain HB101 at a density of 500-2000 colonies per 80 mm plate of L-agar containing 100 μg/ml ampicillin. DNA was transferred from the colonies to nitrocellulose filters and these filters hybridized as described above. Areas on the original plates corresponding to regions of hybridization signals on the filters were picked, then replated and retested by hybridization to isolate single colonies with plasmids containing hybridizing sequences. Positive colonies were further tested by Southern blot analysis of DNA purified from small cultures.

Plasmids purified from hybridization-positive colonies were digested with a variety of restriction enzymes and the resulting fragments analyzed by Southern blot analysis using the same hybridization probes in order to identify restriction fragments of size suitable for DNA sequence analysis. Fragments thus identified were purified by agarose gel electrophoresis and cloned into appropriate MP18 and MP19 vectors. DNA sequence analysis was then performed.

Isolation of Kluyveromyces α-factor

The first 10 amino acids of the K. lactis α-factor showed a definite homology to that from S. cerevisiae, with 6 identical residues. This sequence is shown below:
Trp-Ser-Trp-Ile-Thr-Leu-Arg-Pro-Gly-Gln This protein sequence was used to design a set of oligonucleotides deduced to be complementary to the structural gene for the corresponding structural gene as shown in FIG. 10. Oligonucleotides including all of the possible codons for a segment of the α-factor peptide were sythesized as 2 pools of 96 and 48 different molecules.

These 2 pools were radioactively labelled and were each used to probe a Southern blot of restriction digests of K. lactis DNA Pool #2 gave strong hybridization to a single fragment and much weaker hybridization to a second fragment in several different digests. Thus, pool 2 was chosen to screen plasmid libraries of K. lactis genomic DNA.

Use of these probes to screen plasmid libraries resulted in the isolation of a number of hybridizing clones. DNA sequence analysis of one of these clones, αfk18b, showed it encodes an α-factor related peptide which bears a strong similarity to the precursor of the S. cerevisiae α-factor peptide. The hybridizing segment was located on a PstI-EcoRI fragment of about 1000 bp. The sequence of this fragment is shown in FIG. 11. The K. lactis precursor contains only 2 sites for the addition of N-linked carbohydrate chains. In addition, the spacers of the K. lactis repeats are longer than those of the S. cerevisiae repeats and show a more diverse sequence with the pattern X-Ala/Pro rather than the Glu/Ala-Pro sequences found in S. cerevisiae. A comparison of the DNA sequences showed a strong degree of homology throughout the coding region.

Construction of Plasmids

Figure 12:
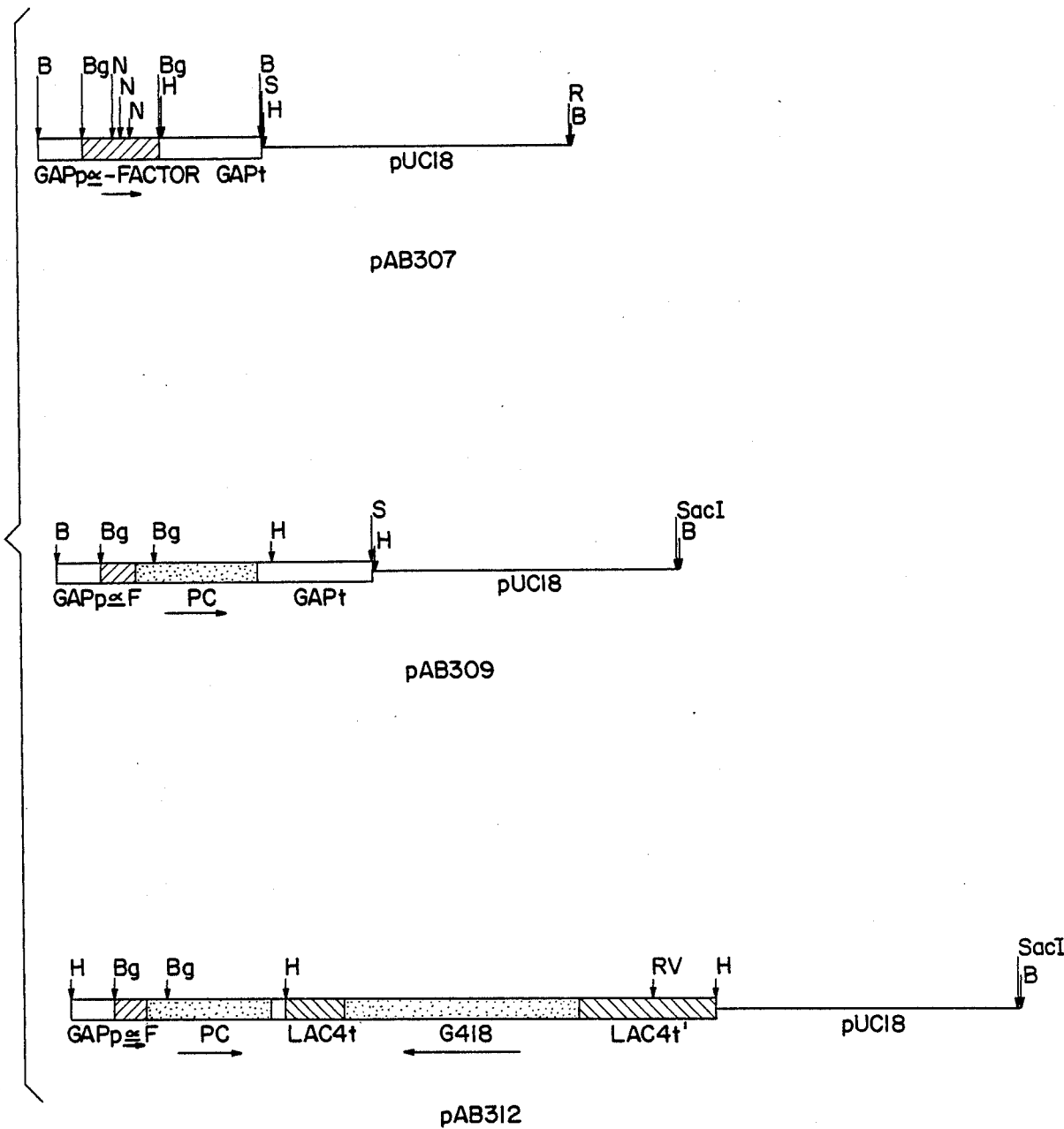
FIG. 12 is a description of plasmids employed for expression of the fusion α-factor signal sequence and prochymosin structural gene.

A series of plasmids (shown in FIG. 12) were constructed in order to provide a fusion of the K. lactis α-factor leader to prochymosin expressed under the transcriptional control of a strong promoter.

pAB307: A 673 bp SspI-EcoRI fragment from αfk18b (FIG. 11) was modified by filling the EcoRI overhang by Klenow enzyme and addition of BglII linkers to the blunt ends. This fragment was then inserted into a BglII site joining the promoter and terminator regions of the S. cerevisiae glyceraldehyde-3-phosphate dehydrogenase gene (GAPDH). This cassette was cloned as a BamHI fragment in pUC18, resulting in pAB307.

pAB309: Fusion of sequences encoding the α-leader and bovine prochymosin was then performed. First pAB307 was digested with NcoI and the cohesive ends made blunt by treatment with mung bean nuclease. The resulting product was then digested with SalI. To this was ligated a 2000 bp EcoRV-SalI fragment containing sequences encoding prochymosin and the *S. cerevisiae* transcriptional termination region. This fragment was derived from plasmid pJS111 in which a XbaI-BamHI adaptor had been added to the 5' end of a fragment containing prochymosin cDNA fused to the *S. cerevisiae* GAPDH transcriptional termination region. This ligation mixture was used to transform *E. coli* strain HB101 and a transformant carrying the plasmid pAB309 was isolated. The sequences around the junction of this fusion are shown in FIG. 13 and the sequence of the entire BamHI insert of pAB309 is shown in FIG. 14.

pAB312a: In order to obtain transformation of *K. lactis* strains, a 3600 bp HindIII fragment derived from pGB901 was inserted into pAB309 producing plasmid pAB312a. The HindIII fragment contains the 3' region of the *K. lactis* LAC4 gene and a fusion of the *S. cerevisiae* ADH1 promoter to the bacterial G418-resistance structural gene.

pAB313 and pAB314: A 1900 bp SacI-HindIII was isolated from pAB309 and cloned into MP19 (Yanisch-Perron et al., *Gene* (1985) 33:103). Single-stranded phage DNA was prepared and used as a template for invitro mutagenesis with one of the two oligonucleotide primers shown in FIG. 15. The M13 · phage MP19/αk11.5 and MP19/αk12.2 were prepared using Primer #1 and Primer #2, respectively.

Double-stranded RF DNA was prepared from these phage, and 1100 bp SacI-StuI fragments isolated from each. These fragments were ligated to a 7100 bp SacI-StuI fragment from pAB312. The resulting plasmids pAB313 and pAB314 were isolated with the sequence alterations illustrated in FIG. 13.

Transformation of Kluyveromyces

Plasmid pAB312a was digested with EcoRV (to target integration to the LAC4 region of the *K. lactis* genome) and was then used to transform *K. lactis* strain 2UV21 (a ura3 trp1 lac4 [kil⁰]) to G418 resistance.

The plasmids pAB313 and pAB314 were used to transform strain 2UV21 to G418 resistance. Cultures of transformants 2UV21::pAB312, 2UV21::pAB313 and 2UV21::pAB314 were grown and culture supernatants assayed for chymosin activity as above.

A number of these transformants, as well as an untransformed control strain, were grown for 36 hours in 1 ml of medium composed of 1% yeast extract, 2% peptone, 2% glucose, 0.17% yeast nitrogen base, 50 μg/ml tryptophan and 50 μg/ml uracil. Culture supernatants were then assayed for chymosin activity after acid activation. All of the transformants were found to secrete activatable chymosin. The results are shown below.

TABLE 9

Secretion of Prochymosin in Kluyveromyces

| Strain | Host | Plasmid | Chymosin Activity (relative units/ml culture) |
|---|---|---|---|
| 2UV21 | 2UV21 | — | <2 |
| KRN303-1 | 2UV21 | pAB312 | 256 |
| KRN304-4 | 2UV21 | pAB313 | 175 |
| KRN305-2 | 2UV21 | pAB314 | 206 |

Each of the transformants was found to secrete a single prochymosin-related species as judged by SDS polyacrylamide gel electrophoresis of trichloroacetic acid-precipitated culture supernatants. The prochymosin-related protein secreted by pAB312 transformants appeared to be of slightly higher molecular weight than those secreted by pAB313 and pAB314 transformants as determined by electrophoretic mobility.

The major species secreted by KRN303-1 and KRN304-4 were purified by preparative SDS polyacrylamide gel electrophoresis and subjected to gas phase amino acid sequence analysis. The N-terminal sequences of these species are given below.

KRN303-1

```
   1                5                  10                 15
Glu—Ala—Asp—Ala—Ser—His—His—Met—Ala—Glu—Ile—Thr—Arg—Ile—Pro
```

KRN304-4

```
   1                5
Ala—Glu—Ile—Thr—Arg—Ile
```

These results indicate that the prochymosin-related species secreted by KRN303-1 has undergone no processing of the amino-terminal spacer sequence, while the species secreted from KRN304-4 has the authentic mature prochymosin amino terminus.

Example 24

Kluyveromyces SD11 lac4 trp1 expressing preprothaumatin and its various maturation forms after being transformed with plasmid pURK 528-01 containing the structural gene encoding preprothaumatin, the KARS-2 sequence from *K. lactis*, the glyceraldehyde-3-phosphate dehydrogenase promoter from *S. cerevisiae* and the TRP1 gene from *S. cerevisiae*

This Example comprises a number of steps, the most essential of which are:

1. Isolation of clones containing the glyceraldehyde-3-phosphate dehydrogenase (GAPDH) operon of *S. cerevisiae*

A DNA pool of the yeast *S. cerevisiae* was prepared in the hybrid *E. coli*-yeast plasmid pFL (Chevallier et al, *Gene* (1980) 11:11–19) by a method similar to the one described by Carlson and Botstein, *Cell* (1982) 28:145–154. Purified yeast DNA was partially digested with restriction endonuclease Sau3A and the resulting DNA fragments (with an average length of 5 kb) were ligated by T4 DNA ligase in the dephosphorylated BamHI site of pFL 1. After transformation of CaCl$_2$-treated *E. coli* cells with the ligated material, a pool of about 30,000 ampicillin resistant clones was obtained.

The clones were screened by a colony hybridization procedure (Thayer, *Anal. Biochem.* (1979) 98:60–63) with a chemically synthesized, $^{32}$P-labeled oligomer with the sequence 5'TACCAGGAGACCAACTT3'.

According to data published by J. P. Holland and M. J. Holland (*J. Biol. Chem.* (1980) 225:2596–2605) this oligomer is complementary with the DNA sequence encoding amino acids 306–310 (the wobble base of the last amino acid was omitted from the oligomer) of the GAPDH gene. Using hybridization conditions described by Wallace et al, *Nucleic Acid Res.* (1981) 9:879–894, six positive transformants could be identified. One of these harbored plasmid pFL 1-33. The latter plasmid contained the GAPDH gene including its promoter/ regulation region and its transcription termination/ polyadenylation region. The approximately 9 kb long insert of pF2 1-33 has been characterized by restriction enzyme analyses (FIG. 16) and partial nucleotide sequence analysis (FIGS. 17 and 18).

Figure 16:
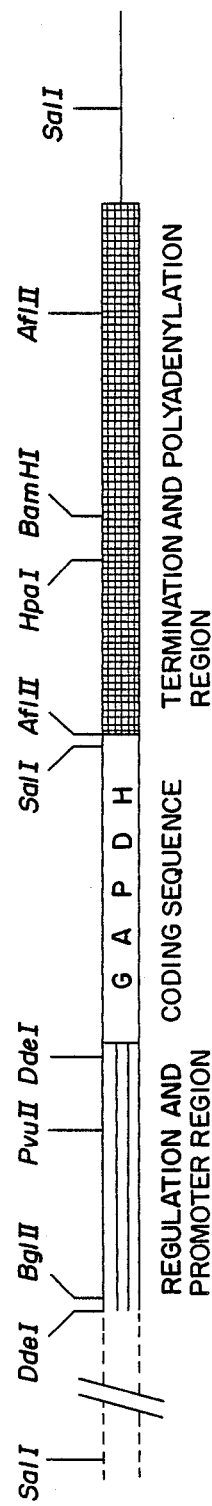
FIG. 16 is a restriction map of the insert in pF2 1-33.

2. Isolation of the GAPDH promoter/regulation region and its introduction into a preprothaumatin encoding plasmid On the basis of the restriction enzyme analysis and the nucleotide sequence data of the insert of plasmid pFL 1-33, the DNA initiation/regulation region of the GAPDH gene was isolated as an 800 nucleotide long DdeI fragment. To identify this promoter fragment, plasmid pFL 1-33 was digested with SalI and the three resulting DNA fragments were subjected to a Southern blot hybridization test with chemically synthesized oligomer (Southern, *J. Mol. Biol.* (1975) 98:503–517). A positively hybridizing 4.3 kb long restriction fragment was isolated on a preparative scale by electroelution from a 0.7% agarose gel and was then cleaved with DdeI. Of the resulting DdeI fragments, only the largest one has a recognition site for PvuII, a cleavage site located within the GADPH promoter region (FIG. 16). The largest DdeI fragment was isolated and incubated with Klenow DNA polymerase and 4 dNTP's (Davis et al., *Gene* (1980) 10:205–218) to generate a blunt-ended DNA molecule. After extraction of the reaction mixture with phenol/chloroform (50/50 v/v), passage of the aqueous layer through a Sephadex G50 column and ethanol precipitation of the material present in the void volume, the DNA fragment was joined to the $^{32}$P-labeled EcoRI linker 5'GGAATTCC3' by incubation with T4 DNA ligase. Using the Klenow polymerase reaction and subsequent ligation of the EcoRI linker, the original DdeI sites were reconstructed at the end of the promoter-containing fragment.

To inactivate the ligase, the reaction mixture was heated to 65° C. for 10 min, then sodium chloride was added (final concentration 50 mM) and the whole mix was incubated with EcoRI. Incubation was terminated by extraction with phenol/chloroform. The DNA was precipitated twice with ethanol, resuspended and then ligated into a suitable vector molecule. Since the DdeI promoter-containing fragment has EcoRI sites, it can easily be introduced into the EcoRI site of pUR528 (Edens et al., *Gene* (1982) 18:1–12) to create a plasmid in which the yeast GAPDH promoter is adjacent to the structural gene encoding preprothaumatin. The latter plasmid was obtained by cleavage of pUR528 with EcoRI, treatment of the linearized plasmid molecule with calf intestinal phosphatase to prevent self-ligation, and incubation of each of these vector molecules as well as the purified DdeI promoter fragment with T4 DNA ligase Transformation of the various ligation mixes in CaCl$_2$-treated *E. coli* HB101 cells yielded several ampicillin resistant colonies. From some of these colonies plasmid DNA was isolated (Birnboim and Doly, *Nucleic Acids Res.* (1979) 7:1513–1523) and incubated with PvuII to test the orientation of the insert.

Figure 19:
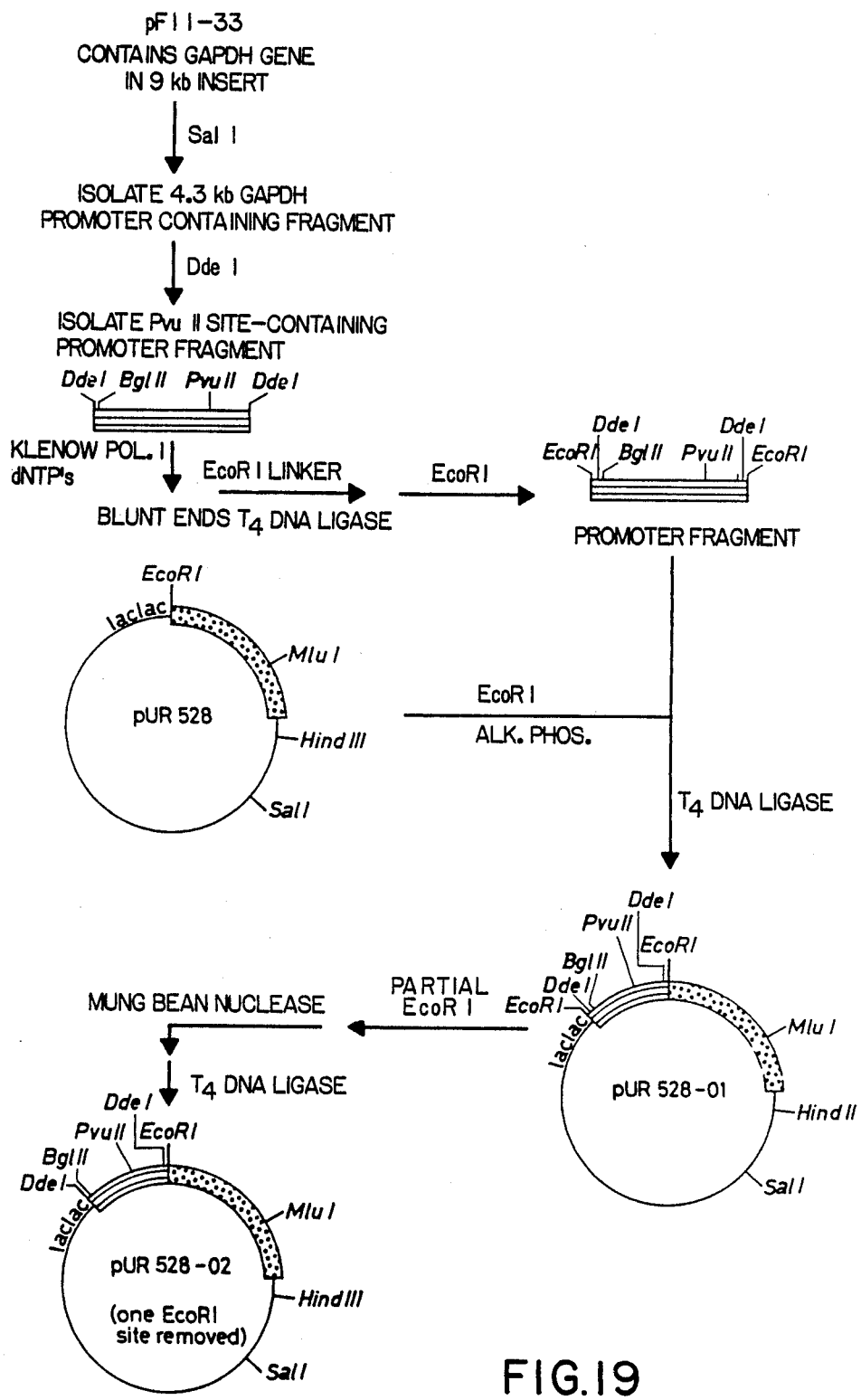
FIG. 19 is a flow diagram of the preparation of pUR528-02.

In the naming of the plasmids, plasmids containing the EcoRI (DdeI) GAPDH promoter fragment in the correct orientation (i.e. transcription from the GAPDH promoter occurs in the direction of a downstream located structural gene) are indicated by the addendum-01 to the original code of the plasmid (for example pUR528 is changed into pUR528-01; see FIG. 19).

To facilitate manipulation of plasmids containing the EcoRI promoter fragment, one of the two EcoRI sites was destroyed. Two μg of plasmid DNA (e.g. pUR 528-01) was partially digested with EcoRI and then incubated with 5 units mung bean nuclease (obtained from P. L. Biochemicals Inc.) in a total volume of 200 μl in the presence of 50 mM sodium acetate (pH 5.0), 50 mM sodium chloride and 1 mM zinc chloride for 30 min. at room temperature to remove sticky ends. The nuclease was inactivated by addition of SDS to a final concentration of 0.1% (Kowalski et al, *Biochemistry* (1976) 15:4457–4463) and the DNA was precipitated by the addition of 2 volumes of ethanol (in this case the addition of 0.1 volume of 3 M sodium acetate was omitted). Linearized DNA molecules were then religated by incubation with T4 DNA ligase and used to transform CaCl$_2$-treated *E. coli* cells. Plasmid DNA isolated from ampicillinresistant colonies was tested by cleavage with EcoRI and MluI for the presence of a single EcoRI site adjacent to the thaumatin gene (see FIG. 19).

Plasmids containing the GAPDH promoter fragment but having only a single EcoRI recognition site adjacent to the ATG initiation codon of a downstream located structural gene are referred to as −02 type plasmids (for example: pUR 528-01 is changed into pUR 528-02; see FIG. 19).

3. Reconstitution of the original GAPDH promoter/regulation region in plasmids encoding preprothaumatin by introduction of a synthetic DNA fragment As shown by the nucleotide sequence depicted in FIG. 20, the EcoRI (DdeI) GAPDH promoter fragment contains the nucleotides −850 to −39 of the original GAPDH promoter/regulation region. Not contained in this promoter fragment are the 38 nucleotides preceding the ATG initiation codon of the GAPDH encoding gene. The latter 38-nucleotide long fragment contains the PuCACACA sequence, which is found in several yeast genes. Said PuCACACA sequence situated about 20 bp upstream of the translation start site (Dobson et al, *Nucleic Acids Res.* (1982) 10:2625–2637) provides the nucleotide sequence upstream of the ATG codon which is optimal for protein initiation (Kozak, *Nucleic Acids Res.* (1981) 9:5233–5252). Moreover, these nucleotides allow the formation of a small loop structure which might be involved in the regulation of expression of the GAPDH gene. On this basis, introduction of the 38 nucleotides in between the DdeI promoter-fragment and the ATG codon of a downstream located structural gene was considered necessary to improve promoter activity as well as translation initiation.

As outlined in FIG. 21, the missing DNA fragment was obtained by the chemical synthesis of two partially overlapping oligomers. The SacI site present in the overlapping part of the 2 oligonucleotides was introduced for two reasons: (i) to enable manipulation of the nucleotide sequence immediately upstream of the ATG codon including the construction of poly A-tailed yeast expression vectors: (ii) to give a cleavage site for an enzyme generating 3'-protruding ends that can easily and reproducibly be removed by incubation with T4 DNA polymerase in the presence of the 4 dNTP's. Equimolar amounts of the two purified oligomers were phosphorylated at their 5'-termini, hybridized (Rossi et al, *J. Biol. Chem.* (1982) 257:9226-9229) and converted into a double-stranded DNA molecule by incubation with Klenow DNA polymerase and the 4 dNTP's under conditions which have been described for double-stranded DNA synthesis (Davis et al., *Gene* (1980) 10:205-218). Analysis of the reaction products by electrophoresis through a 13% acrylamide gel followed by autoradiography showed that more than 80% of the starting single-stranded oligonucleotides were converted into double-stranded material. The DNA was isolated by passage of the reaction mix over a Sephadex G50 column and ethanol precipitation of the material present in the void volume. The DNA was then phosphorylated by incubation with polynucleotides cleaved off in the latter reaction and the reaction mix subjected to two precipitations with ethanol.

Figure 20:
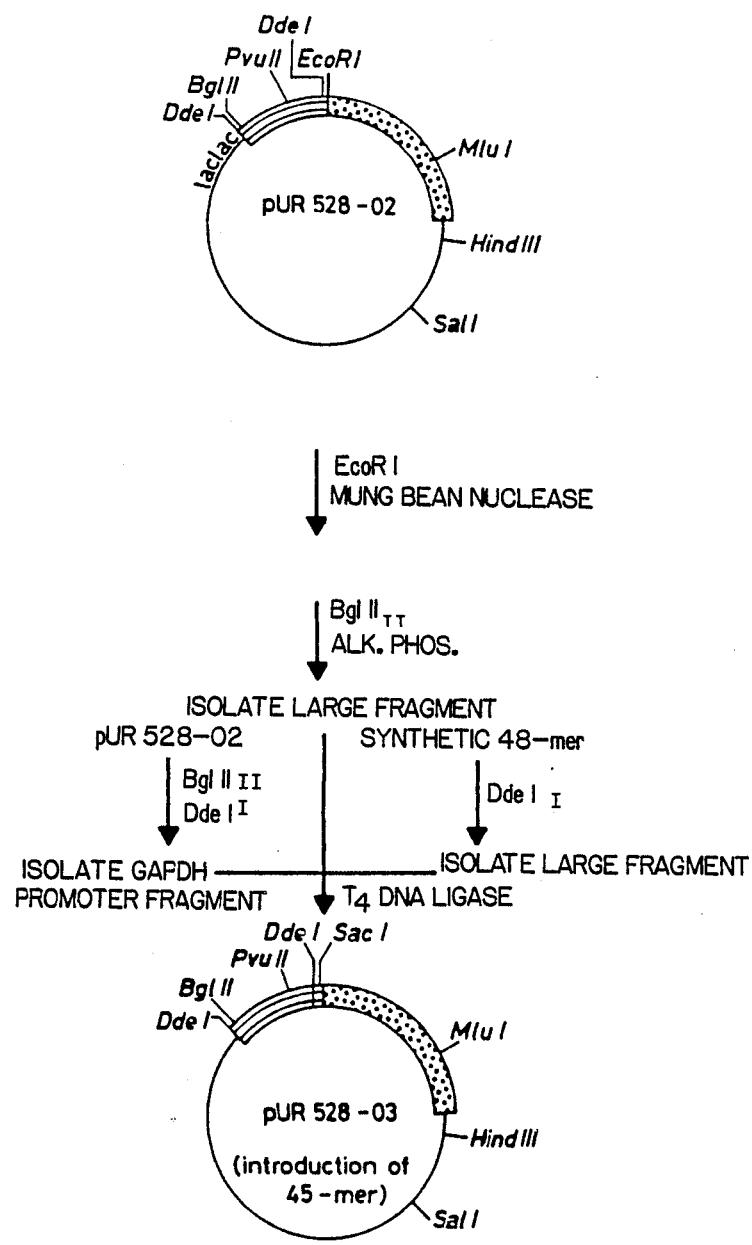
FIG. 20 is a flow diagram of the preparation of pUR528-03.

As shown in FIG. 20, cloning of the resulting synthetic DNA fragment was carried out by the simultaneous ligation of this fragment and a BglII-DdeI GAPDH promoter regulation fragment in a vector molecule from which the EcoRI site preceding the ATG initiation codon was removed by mung bean nuclease digestion (see Step 2). The BglII-DdeI promoter/regulation fragment was obtained by digestion of plasmid pUR528-02 with DdeI and BglII. Separation of the resulting restriction fragments by electrophoresis through a 2% agarose gel and subsequent isolation of the fragment from the gel yielded the purified 793 nucleotides long promoter/ regulation fragment. In the plasmid pUR528-02 the nucleotide sequence preceding the ATG codon is 5'-GAATTC(T)ATG-3' (EPA 54330 and EPA 54331), which is different from the nucleotide sequence given by Kozak (*Nucleic Acids Res.* (1981) 9:5233-5252). Since our aim was to reconstitute the original GAPDH promoter/regulation/protein initiation region as accurately as possible, the EcoRI site was removed in order to ligate the synthetic DNA fragment to the resulting bluntend. Removal of the EcoRI site was accomplished by mung bean nuclease digestion of EcoRI-cleaved pUR528-02 DNA.

Subsequently, the plasmid DNA was digested with BglII and incubated with phosphatase. After separation of the two DNA fragments by electrophoresis through a 0.7% agarose gel, the largest fragment was isolated and used as the vector into which the BglII-DdeI promoter fragment as well as the DdeI-treated-synthetic DNA fragment were ligated. Plasmids in which the DdeI promoter/regulation fragment together with the SacI recognition site containing synthetic DNA fragment are introduced are indicated by the addendum-03 (for example: pUR528-02 is changed into pUR528-03).

Figure 22:
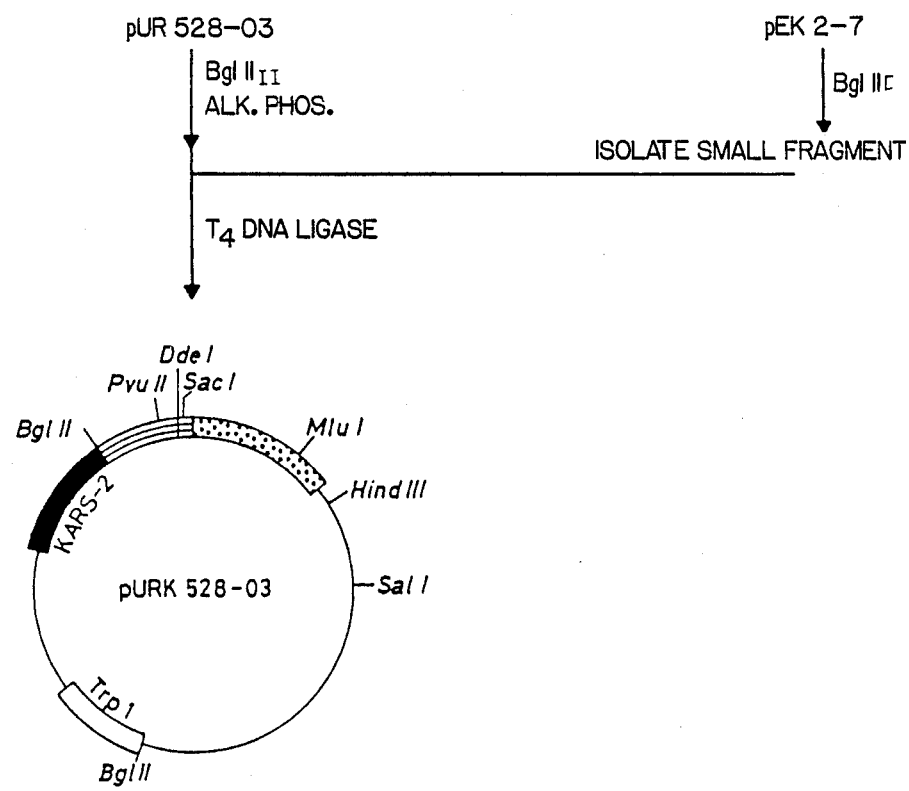
FIG. 22 is a flow diagram of the preparation of pURK528-03.
Figure 23:
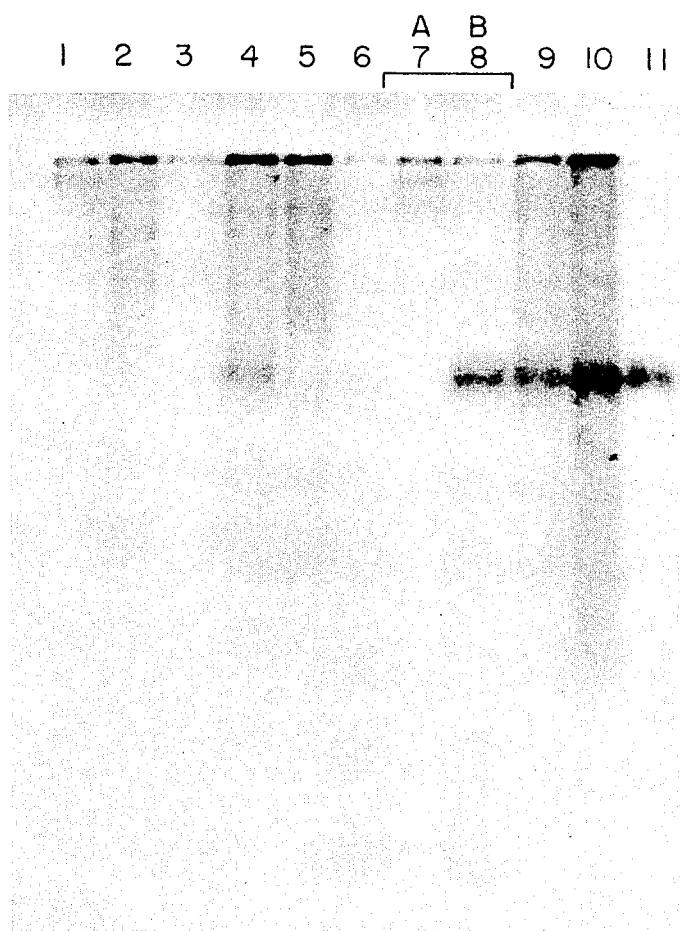
FIG. 23 shows an analysis of $^{35}$S-labeled proteins from *K. lactis* SD11 cells transformed with pURK528-03.

4. Introduction of the KARS-2 replicon from *K. lactis* and the TRP1 gene from *S. cerevisiae* in preprothaumatin encoding plasmids The KARS-2 replicon and the TRP1 gene were excised from pEK2-7 by digestion with BglII, followed by isolation from an 0.7% agarose gel of the 3.5 kb fragment. This purified fragment was inserted in the dephosphorylated BglII cleavage site of pUR528-03 by incubation with T4 DNA ligase. Transformation of the ligation mix in *E. coli* yielded plasmid pURK528-03 (FIG. 22). Transformants generated by the introduction of plasmid pURK 528-03 into *K. lactis* SD11 cells by the Li+ method were shown to synthesize thaumatin-like proteins assayed as described by L. Edens et al., *Gene* (1982) 18:1-12 (see FIG. 23).

The above results demonstrate that one can obtain efficient, convenient expression of exogenous genes in Kluyveromyces strains. Furthermore, the Kluyveromyces strains appear to be particularly useful for providing highly efficient secretion and processing of a wide variety of proteins, as illustrated by the results with prochymosin. Constructs and vectors are provided which allow for the introduction of an exogenous gene under the regulatory control of efficient promoters in Kluyveromyces and, as desired, joining to signal sequences which provide for translocation of the exogenous gene, particularly secretion. Thus, a fermentation system is provided for commercial production of a wide variety of exogenous proteins in an active or activatable form.

The following organisms have been deposited with the American Type Culture Collection on June 30, 1987: 2UV21, ATCC Accession No. 20855; KRN201-6, ATCC Accession No. 20854; HB101 pAB307, ATCC Accession No. 67454; HB101 pAB312, ATCC Accession No. 67455.

Although the foregoing invention has been described in some detail by way of illustration and example for purposes of clarity of understanding, it will be obvious that certain changes and modifications may be practiced within the scope of the appended claims.

What is claimed is:

1. A method for transforming Kluyveromyces yeast cells which comprises:

pretreating said yeast cells with a chaotropic ion at a concentration of about 2 mM to about 1 M then treating said yeast cells with about 25-50% polyethylene glycol, wherein said pretreating and said treating is for about 5 to 120 minutes;

incubating said yeast cells with a DNA construct at about 20° C. to 35° C. for about 5 to 60 minutes;

heating said yeast cells with polyethylene glycol at about 35° C. to about 45° C. for about 1 to 10 minutes; and growing said yeast cells.

2. A method according to claim 1, wherein said chaotropic ion is lithium at a concentration of about 2 mM to about 1 M.

3. A method according to claim 2, wherein said lithium ion concentration is about 0.1 M.

4. A method according to claim 1, wherein said DNA construct comprises in the direction of transcription, a transcriptional initiation regulatory region functional in said host cell; a DNA sequence encoding a polypeptide of interest; and a transcriptional termination regulatory region functional in said host cell.

5. A method according to claim 4, wherein said DNA construct further comprises at least one of a selection marker, a replication system for autonomous replication of said DNA sequence, or a transformation efficiency enhancing sequence.

6. A method according to claim 5, wherein said selection marker is resistance to G418.

7. A method according to claim 4, wherein said DNA construct further comprises a signal sequence functional in said yeast cells joined in reading frame to said DNA sequence.

8. A method according to claim 5, wherein said replication system is a yeast 2 micron replication sequence.

9. A method according to claim 4, wherein said DNA construct further comprises a KARS.

10. A method according to claim 9, wherein said KARS is a KARS12 or KARS2.

11. A method according to claim 5, wherein said replication system is an autonomously replicating sequence (ARS).

12. A method for obtaining transformed Kluyveromyces yeast cells which comprises:
pretreating said yeast cells with a chaotropic ion at a concentration of about 2 mM to about 1 M then treating said yeast cells with about 25–50% polyethylene glycol, wherein said pretreating and said treating is for about 5 to 120 minutes;
incubating said yeast cells with a DNA construct at about 20° C. to 35° C. for about 5 to 60 minutes, wherein said DNA construct comprises a DNA sequence which confers resistance to an antibiotic;
heating said yeast cells with polyethylene glycol at about 35° C. to about 45° C. for about 1 to 10 minutes;
growing said yeast cells in the presence of a sufficient concentration of said antibiotic whereby transformants are selected for; and
isolating said transformants.

13. A method according to claim 12, wherein said antibiotic is G418.

14. A method for obtaining transformed Kluyveromyces yeast cells which comprises:
contacting Kluyveromyces cells treated with a chaotropic ion and a DNA construct comprising a selection marker in the presence of a fusant under fusing conditions; and
growing said cells under conditions whereby transformants comprising said DNA construct are selected for; and
isolating said transformants.

15. A method according to claim 14, wherein said Kluyveromyces cells are protoplasts.

16. A method according to claim 15, wherein said chaotropic ion is calcium.

* * * * *

UNITED STATES PATENT AND TRADEMARK OFFICE
CERTIFICATE OF CORRECTION

PATENT NO. : 4,943,529

DATED : July 24, 1990

INVENTOR(S) : J. A. Van den Berg, et al.

It is certified that error appears in the above-identified patent and that said Letters Patent is hereby corrected as shown below:

Facing Page, [75] change "Inventors: Johan A. Van den Berg, Ad Reeuwijk; Albert J. J. Van Ooyen, AR Voorburg, Krijn Rietveld, TL Vlaardingen, all of Netherlands"

to --Inventors: Johan A. Van den Berg, Reeuwijk, Netherlands; Albert J. J. Van Ooyen, Voorburg, Netherlands; Krijn Rietveld, Vlaardingen, Netherlands; Cornelis P. Hollenberg, Dusseldorf, Federal Republic of Germany; Sunil Das, Dusseldorf, Federal Republic of Germany; Albert de Leeuw, Pijnacker, Netherlands--.

Facing Page, [73] before "Delft" insert --2600 MA--.
Facing Page, [21] change "78,539" to --078,539--.
Column 6, line 30, change "or" to --or a --.
Column 6, line 54, change "associated with" to --related to--.
Column 6, line 65-66, change "provide" to --provides--.
Column 10, line 48, change "strain DG75 (hsdS1leu-6 ara-14 galK2 xyl-5 15 mt-1" to --strain DG75 (hsdS1 leu-6 ara-14 galK2 xyl-5 mt-1--.
Column 11, line 36, change "Kluyveromyces lactis" to --_Kluyveromyces lactis_--.
Column 11, line 38, change "Kluyveromyces lactis" to --_Kluyveromyces lactis_--.
Column 12, lines 18-19, change "(see Table, p. 21)" to --(see Table 1)--.
Column 12, line 27, change "Kluyveromyces lactis" to --_Kluyveromyces lactis_--.
Column 12, line 49, change "Kluyveromyces lactis" to --_Kluyveromyces lactis_--.
Column 13, line 16, change "Kluyveromyces lactis" to --_Kluyveromyces lactis_--.

UNITED STATES PATENT AND TRADEMARK OFFICE
CERTIFICATE OF CORRECTION

Page 2 of 2

PATENT NO. : 4,943,529

DATED : July 24, 1990

INVENTOR(S) : J. A. Van den Berg, et al.

It is certified that error appears in the above-identified patent and that said Letters Patent is hereby corrected as shown below:

Column 13, line 25, "2% glucose..." should not begin a new paragraph and should follow "and" in line 24.

Column 13, line 43, change "Kluyveromyces fragilis" to --*Kluyveromyces fragilis*--.

Column 13, line 66, change "*method as described in Example*" to --method as described in Example--.

Column 14, line 13, change "Kluyveromyces lactis" to --*Kluyveromyces lactis*--.

Column 16, line 50, change "Kluyveromyces lactis" to --*Kluyveromyces lactis*--.

Column 19, line 14, change "Kluyveromyces lactis" to --*Kluyveromyces lactis*--.

Column 24, line 7, change "*Lactis*" to --*lactis*--.

Signed and Sealed this

Twenty-ninth Day of October, 1991

Attest:

HARRY F. MANBECK, JR.

*Attesting Officer*          *Commissioner of Patents and Trademarks*